United States Patent [19]
Hutchins et al.

[11] Patent Number: 5,863,527
[45] Date of Patent: Jan. 26, 1999

[54] PERSONAL CARE COMPOSITIONS

[75] Inventors: Thomas Allen Hutchins, Cincinnati; Michael Albert Snyder, Mason, both of Ohio; Mario Paul Clarizia, Iowa City, Iowa

[73] Assignee: The Proctor & Gamble Company, Cincinnati, Ohio

[21] Appl. No.: 833,820

[22] Filed: Apr. 9, 1997

Related U.S. Application Data

[63] Continuation-in-part of Ser. No. 708,334, Sep. 4, 1996, abandoned.

[51] Int. Cl.$^6$ .................................. A61K 7/04; A61K 7/48
[52] U.S. Cl. .................. 424/70.16; 424/401; 424/78.18; 424/78.26; 424/70.1; 424/70.2; 424/70.12; 424/70.19; 424/70.22; 424/70.27; 424/70.28; 514/937; 514/944
[58] Field of Search ................................. 421/401, 78.18, 421/78.24, 70.1, 70.2, 70.12, 70.16, 70.19, 70.22, 70.27; 514/937, 944

[56] References Cited

U.S. PATENT DOCUMENTS

| | | | |
|---|---|---|---|
| 3,208,211 | 9/1965 | Oppliger | 167/87 |
| 3,957,970 | 5/1976 | Korkis | 424/70 |
| 4,030,512 | 6/1977 | Papantoniou et al. | 132/7 |
| 4,136,250 | 1/1979 | Mueller et al. | 528/29 |
| 4,185,087 | 1/1980 | Morlino | 424/70 |
| 4,277,595 | 7/1981 | Deichert et al. | 528/26 |
| 4,479,893 | 10/1984 | Hirota et al. | 252/542 |
| 4,563,347 | 1/1986 | Starch | 424/70 |
| 4,601,902 | 7/1986 | Fridd et al. | 424/70 |
| 4,654,161 | 3/1987 | Kollmeier et al. | 252/174.15 |
| 4,659,777 | 4/1987 | Riffle et al. | 525/100 |
| 4,663,413 | 5/1987 | Ward et al. | 528/26 |
| 4,689,383 | 8/1987 | Riffle et al. | 528/12 |
| 4,693,935 | 9/1987 | Mazurek | 428/352 |
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,814,402 | 3/1989 | Nakashima et al. | 526/245 |
| 4,874,604 | 10/1989 | Sramek | 424/47 |
| 4,902,499 | 2/1990 | Bolich, Jr. et al. | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,988,506 | 1/1991 | Mitra et al. | 424/81 |
| 5,021,477 | 6/1991 | Garbe et al. | 424/70 |
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,166,276 | 11/1992 | Hayama et al. | 525/329 |
| 5,219,560 | 6/1993 | Suzuki et al. | 424/63 |
| 5,229,435 | 7/1993 | Sakai et al. | 523/105 |

FOREIGN PATENT DOCUMENTS

| | | |
|---|---|---|
| 0 117 360 | 12/1983 | European Pat. Off. . |
| 0 116 207 | 8/1984 | European Pat. Off. . |
| 0 274 086 | 7/1988 | European Pat. Off. . |
| 0 408 311 A2 | 7/1990 | European Pat. Off. . |
| 0 403 282 | 12/1990 | European Pat. Off. . |
| 0 412 745 A1 | 2/1991 | European Pat. Off. . |
| 56-092-811 | 7/1981 | Japan . |
| 56-6129-300 | 10/1981 | Japan . |
| 4-359912 | 6/1991 | Japan . |
| 4-359913 | 6/1991 | Japan . |
| 4-360812 | 6/1991 | Japan . |
| WO 88/05060 | 7/1988 | WIPO . |
| WO 92/13566 | 8/1992 | WIPO . |

*Primary Examiner*—Jyothsna Venkat
*Attorney, Agent, or Firm*—Darryl C. Little; George W. Allen

[57] ABSTRACT

The present invention relates to personal care compositions comprising a copolymer complex and a volatile, hydrophobic solvent component for solubilizing or dispersing the copolymer complex. The copolymer complex is formed by complexing a fatty amine with a copolymer, wherein the copolymer comprises a hydrophobic monomer, a hydrophilic monomer such that at least 1%, by weight of the total copolymer, comprises hydrophilic monomers bearing acidic functional groups, and optionally a hydrophobic macromonomer.

18 Claims, No Drawings

PERSONAL CARE COMPOSITIONS

This is a continuation-in-part of application Ser. No. 08/708,334, filed on Sep. 4, 1996 now abandoned.

TECHNICAL FIELD

The present invention relates to personal care compositions comprising a copolymer complex and a volatile, hydrophobic solvent component for solubilizing or dispersing the copolymer complex. The copolymer complex is formed by complexing a fatty amine with a copolymer, wherein the copolymer comprises a hydrophobic monomer, a hydrophilic monomer such that at least 1%, by weight of the total copolymer, comprises hydrophilic monomers bearing acidic functional groups, and optionally a hydrophobic macromonomer. These compositions provide improved delivery, deposition and retention to the hair and skin.

BACKGROUND OF THE INVENTION

The rheological, holding, and film-forming properties of polymers and copolymers have contributed immensely to their usefulness in a wide variety of personal care compositions. Products containing polymers include hairsprays, shampoos, hair conditioners, skin creams and lotions, make-up products, antiperspirants and deodorants, shaving creams, topical drug compositions, sunscreen products, and the like. Consumers are constantly seeking products providing improved performance benefits.

In their quest to improve upon current products and to create new products, scientists and formulators are continually seeking to develop new key ingredients for such products. Because polymers play such an important role in the formulation of many personal care products, a need exists for new polymers having new and useful properties. In the hair care area, for example, style retention is generally accomplished by application of either permanent chemical alteration products or temporary styling products. A permanent chemical alteration product, which is commonly referred to as a "hair perm," typically involves treating the hair with various sulfur-containing compounds in order to break the disulfide bonds in the hair fibers, thereby enabling one to alter the shape and orientation of the hair fibers. However, hair perm products have the disadvantage of being harsh and damaging to the hair, and of being long-lasting and difficult to reverse. Conversely, temporary styling products generally do not break the chemical bonds in the hair fibers. These temporary styling products typically are in the form of gels, lotions, mousses, or sprays containing polymeric resins or gums for coating the hair fibers and bonding them together. Many temporary styling products are inconvenient to use and have the disadvantage of not allowing one to readily restyle the hair after the initial application and styling is completed, without further application of additional product. It would be preferable to deliver styling and hold benefits using rinse-off products such as conditioners and shampoos. These types of rinse-off products, however, require styling agents that are substantive to the hair and not readily removed during the rinsing process. Especially useful styling and hold agents for rinse-off compositions are hydrophobic polymeric materials. Such hydrophobic materials, however, may cause a buildup of an unsightly visible residue on the hair with repeated usage. This residue can eventually completely surround the hair shaft and can be difficult to remove with normal shampooing. Therefore, the need exists for improved compositions for providing temporary styling and hold of human hair without the residue and negatives often associated with such compositions. Similarly, a need remains for film-forming skin compositions which are readily washed off by soap and water.

It has surprisingly been found that hair care products comprising a copolymer complex comprising a copolymer having at least one acid functional monomer and at least one fatty amine complexed with the acid functional monomer provide excellent temporary styling and hold benefits in addition to improved "wash off" characteristics. The copolymer complex of the present invention is soluble or dispersible in and readily deposited by hydrophobic solvent components, yet easily washed away by aqueous surfactant solutions. These compositions can be made into any of a number of conventional forms including, but not limited to, shampoos, conditioners, mousses, gels, lotions, sprays and the like.

In addition to the afore-mentioned hair care benefits, it has been found that the copolymer complex and volatile, hydrophobic solvent component of the present invention are also useful for incorporation into a wide variety of cosmetic and pharmaceutical compositions for topical application to the skin. These materials provide topical compositions which are more easily and uniformly spread upon the skin, which feel good upon the skin, and yet are highly substantive. Furthermore, these compositions are useful for providing occlusion to enhance the penetration of a wide variety of cosmetic and pharmaceutical actives into the skin, or alternatively, through the skin for systemic delivery.

The compositions of the present invention comprise a copolymer complex and a volatile, hydrophobic solvent component suitable for application to the hair or skin. The copolymer complex comprises a copolymer having at least one acid functional monomer and at least one fatty amine complexed with the acid functional monomer.

It is therefore an object of the present invention to provide copolymer complexes having improved solubility or dispersibility characteristics.

It is another object of the present invention to provide copolymer complexes that are soluble or dispersible in hydrophobic solvent components and yet are readily washed away by aqueous surfactant solutions.

It is another object of the present invention to provide personal care compositions in the form of hair care compositions having improved styling and/or hold properties and having improved aesthetics.

It is another object of the present invention to provide personal care compositions in the form of topical cosmetic and pharmaceutical compositions useful for delivering and retaining a wide variety of cosmetic materials and pharmaceutical actives to and/or through the skin.

It is another object of the present invention to provide rinse off compositions useful for styling and holding hair.

It is another object of the present invention to provide methods for styling and holding the hair.

It is another object of the present invention to provide methods for delivering and retaining to the skin cosmetic materials and pharmaceutical actives.

These and other objects will become readily apparent from the detailed description which follows.

SUMMARY OF THE INVENTION

The compositions of the present invention relate to personal care compositions, comprising:

A.) a copolymer complex comprising:
 a.) a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:
   i) from about 10% to about 99% by weight of the copolymer of one or more hydrophobic A monomer units, wherein the A monomer units are copolymerizble with the B monomer and C macromonomer units;
   ii) from about 1% to about 40% by weight of the copolymer of one or more hydrophilic B monomer units, wherein the B monomer units are copolymerizable with the A monomer and C macromonomer units and wherein at least about 1% by weight of the copolymer, of the B monomer units, are selected from B monomer units having at least one acid functional group; and
   iii) from 0 to about 50% by weight of the copolymer of one or more C macromonomer units wherein the C units are hydrophobic macromonomer units, copolymerizable with the A monomer units and the B monomer units, the C macromonomer units having a number average molecular weight of from about 1,500 to about 50,000; and
   b.) a complexing fatty amine wherein the fatty amine forms a complex with the acid functional group of the B monomer units;
   wherein the weight ratio of the copolymer to the fatty amine is from about 50:1 to about 1:1; and
B.) a volatile, hydrophobic solvent component for the copolymer complex having a boiling point at 1 atmosphere of about 260° C. or less and a solubility parameter of about 8.5 $(cal/cm^3)^{1/2}$ or less
wherein the copolymer complex is soluble or dispersible in the volatile, hydrophobic solvent component.

In further embodiments, the present invention relates to a method of making a personal care composition, comprising the steps of:
   a.) preparing a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:
      i) from about 10% to about 99% by weight of the copolymer of one or more hydrophobic A monomer units, wherein the A monomer units are copolymerizble with the B monomer and C macromonomer units;
      ii) from about 1% to about 40% by weight of the copolymer of one or more hydrophilic B monomer units, wherein the B monomer units are copolymerizable with the A monomer and C macromonomer units and wherein at least about 1% by weight of the copolymer, of the B monomer units, are selected from B monomer units having at least one acid functional group; and
      iii) from 0 to about 50% by weight of the copolymer of one or more C macromonomer units wherein the C units are hydrophobic macromonomer units, copolymerizable with the A monomer units and the B monomer units, the C macromonomer units having a number average molecular weight of from about 1,500 to about 50,000; and
   b.) complexing the copolymer with a fatty amine wherein the weight ratio of the copolymer to the fatty amine is from about 50:1 to about 1:1; and
   c.) dissolving or dispersing the copolymer complex in a volatile, hydrophobic solvent component having a boiling point at 1 atmosphere of about 260° C. or less and a solubility parameter of about 8.5 $(cal/cm^3)^{1/2}$ or less.

In further embodiments, the present invention relates to a personal care composition which or to mixing, comprises:
   A.) a copolymer complex comprising:
      a.) a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:
         i) from about 10% to about 99% by weight of the copolymer of one or more hydrophobic A monomer units, wherein the A monomer units are copolymerizable with the B monomer and C macromonomer units;
         ii) from about 1% to about 40% by weight of the copolymer of one or more hydrophilic B monomer units, wherein the B monomer units are copolymerizable with the A monomer and C macromonomer units and wherein at least about 1% by weight of the copolymer, of the B monomer units, are selected from B monomer units having at least one acid functional group; and
         iii) from 0 to about 50% by weight of the copolymer of one or more C macromonomer units wherein the C units are hydrophobic macromonomer units, copolymerizable with the A monomer units and the B monomer units, the C macromonomer units having a number average molecular weight of from about 1,500 to about 50,000; and
      b.) a complexing fatty amine wherein the fatty amine forms a complex with the acid functional B monomer units
      wherein the weight ratio of the copolymer to the fatty amine is from about 50:1 to about 1:1; and
   B.) a volatile, hydrophobic solvent component for the copolymer complex having a boiling point at 1 atmosphere of about 260° C. or less and a solubility parameter of about 8.5 $(cal/cm^3)^{1/2}$ or less
wherein the copolymer complex is soluble or dispersible in the volatile, hydrophobic solvent component.

Unless otherwise indicated, all percentages and ratios used herein are by weight of the total composition. All weight percentages, unless otherwise indicated, are on an actives weight basis. All measurements made are at 25° C., unless otherwise designated. The invention hereof can comprise, consist of, or consist essentially of, the essential as well as optional ingredients and components described herein.

DETAILED DESCRIPTION OF THE INVENTION

Essential Components

The compositions of the present invention comprise a copolymer complex and a volatile, hydrophobic solvent component suitable for application to the hair and skin, wherein the copolymer complex comprises a copolymer complexed with a fatty amine.

The copolymers of the present invention can include graft copolymers. The term "graft copolymers" is familiar to one of ordinary skill in polymer science and is used herein to describe the copolymers which result by adding or "grafting" a polymeric chemical moiety (i.e. "grafts") onto another polymeric moiety commonly referred to as the "backbone". The backbone typically has a higher molecular weight than the grafts. Thus, graft copolymers can be described as polymers having pendant polymeric side chains, and as being formed from the "grafting" or incorporation of polymeric side chains onto or into a polymer. The polymer to which the grafts are incorporated can be homopolymers or copolymers. The graft copolymers are derived from a variety of monomer units.

The copolymers of the present invention can be prepared from the copolymerization of monomer units and macromonomer units such that the macromonomer units are "grafted" or incorporated into the resulting copolymer. The term "macromonomer" is a term familiar to one of ordinary skill in polymer science, and is used to described a polymeric material containing a polymerizable moiety. In other words, a macromonomer is a macromolecular monomer, which is essentially a high molecular weight type of monomer building block unit which can be used in a polymerization reaction to form polymers with itself; with other monomers, or with other macromonomers.

The term "hydrophilic" is used herein consistent with its standard meaning of having affinity for water, whereas "hydrophobic" is used herein consistent with its standard meaning of lacking affinity for water. As used herein in relation to monomer units and polymeric materials, including the macromonomers, copolymers, and solvents for the copolymers, "hydrophilic" means substantially water soluble. "Substantially water soluble" shall refer to a material that is soluble in distilled (or equivalent) water, at 25° C., at a concentration of 0.2% by weight, and are preferably soluble at 1.0% by weight In contrast, "hydrophobic" means substantially water insoluble. In this regard, "substantially water insoluble" shall refer to a material that is not soluble in distilled (or equivalent) water, at 25° C., at a concentration of 0.2% by weight, and preferably not soluble at 0.1% by weight.

The term "soluble" or "solubility" as used herein, means the capability of a substance to form a solution, i.e., either a true solution or a colloidal solution. A true solution being a uniformly dispersed mixture at the molecular or ionic level, of one or more substances (the solute) in one or more substances (the solvent). These two parts of a solution are called phases. A colloidal dispersion is often called a solution. Since colloidal particles are larger than molecules it is strictly incorrect to call such dispersions solutions; however this term is widely used in the literature. The term "dispersible" or "dispersibility" as used herein, means the capability of a substance to form a dispersion, i.e., a two-phase system where one phase consists of finely divided particles (often in the colloidal size range) distributed throughout a bulk substance, the particles being the disperse or internal phase and the bulk substance the continuous or external phase.

The term "rinse" off or wash off is used herein to mean that the compositions of the present invention are used in a context whereby the composition is ultimately rinsed or washed from the hair and/or skin either after or during the application of the product Nonlimiting examples of rinse-off products of the present invention include hair conditioners, shampoos and soaps.

The term "substantive" or "substantivity" as used herein, means the binding or retention of a chemical or pharmaceutical active to the surface layer of the stratum corneum or to hair.

The term "suitable for application to human hair and skin" as used herein, means that the compositions or components thereof so described are suitable for use in contact with human hair and the scalp and skin without undue toxicity, incompatibility, instability, allergic response, and the like.

The aforementioned definitions shall also apply to other materials so described herein, to the extent any other definitions regarding such materials are consistent with those stated above.

The compositions of the present invention comprise the following essential components.

Copolymer complex

The hair and skin care compositions of the present invention comprise from about 0.25% to about 30%, preferably from about 2% to about 15%, and more preferably from about 2% to about 10%, by weight, based on the weight of the hair and skin care composition, of a copolymer complex. The copolymer complex comprises a copolymer having at least one acid functionalized monomer complexed with a fatty amine.

Copolymer

The copolymer complex of the present invention comprises from about 35% to about 99%, preferably from about 40% to about 90%, and more preferably from about 50% to about 70%, by weight, based on the weight of copolymer complex, of a copolymer. Based on the weight of the overall hair and skin care composition, the copolymer comprises from about 0.1% to about 10%, preferably from about 1% to about 5%, and more preferably from about 1.5% to about 3.5%, by weight.

The copolymers of the present invention have a weight average molecular weight, in grams/mole, of at least about 10,000. There is no upper limit for molecular weight except that which limits applicability of the invention for practical reasons, such as viscosity, processing, aesthetic characteristics, formulation compatibility, etc. The weight average molecular weight is generally less than about 5,000,000, more generally less than about 2,500,000, and typically less than about 1,500,000. Preferably, the weight average molecular weight is from about 10,000 to about 5,000,000, more preferably from about 50,000 to about 2,000,000, even more preferably from about 75,000 to about 1,000,000, and most preferably from about 75,000 to about 500,000.

The copolymers of the present invention are formed from the copolymerization of randomly repeating A monomer units and B monomer units, preferably wherein the A monomers are polymerizable, ethylenically unsaturated monomers selected to meet the requirements of the copolymer. By "polymerizable," as used herein, is meant monomers that can be polymerized using any conventional synthetic techniques. Monomers that are polymerizable using conventional free radical initiated techniques are preferred. The term "ethylenically unsaturated" is used herein to mean monomers that contain at least one polymerizable carbon-carbon double bond (which can be mono-, di-, tri-, or tetra-substituted). The B monomer units are hydrophilic monomers which are copolymerizable with A and selected from polar monomers, preferably having a Tg or a Tm above about −20° C., and wherein at least 1%, by weight of the copolymer, of the hydrophilic B monomer is selected from hydrophilic B monomers having at least one acid functional group. The A monomer and B monomer units form what is termed the backbone of the polymer and can be selected from a wide variety of structures as long as the copolymer has the required properties and meets the molecular weight and other requirements described herein. The copolymers of the present invention may optionally incorporate C macromonomer units. The C macromonomer units are selected from at least one hydrophobic macromonomer unit which contains a polymeric portion and a moiety copolymerizable with the A monomer and the B monomer. The C macromonomer units form hydrophobic side chains on the copolymer.

The copolymers are prepared by the polymerization combination of A and B monomers and can be characterized by the weight percent of the monomers charged to the reaction vessel in which the polymerization reaction is run. C macromonomers may be optionally incorporated into the polymerization reaction.

As will be clear to one skilled in the art and especially from the Examples, the copolymer may have one or more hydrophobic side chains grafted to the backbone. As known in the art, synthetic graft copolymerization processes may produce a mixture of polymer molecules containing no, one, or more than one hydrophobic side chains covalently bonded to and pendant from the polymeric backbone. From knowledge of the amount and number average molecular weight of hydrophobic side chains in a polymer sample, and the number average molecular weight of the polymer sample, it is possible to calculate the average number of hydrophobic side chains per polymer backbone.

The copolymer complex of the present invention, when dried to a film having 0.5% or less of the volatile hydrophobic solvent component, have a Tg or Tm of at least about −20° C., more preferably at least about 20° C., so that the copolymers are not unduly sticky, or "tacky" to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are above about −20° C., more preferably above about 20° C.

The grafted copolymers should satisfy the following criteria:

(1) the polymeric side chain portion is covalently bonded to the backbone portion; and
(2) the number average molecular weight of the polymeric side chain portion is from about 1,500 to about 50,000.

The copolymers of the present invention are prepared by the polymerization combination of A monomers and B monomers. C macromonomers may optionally be incorporated into the polymerization process. The copolymers can be synthesized by free radical polymerization of the monomers and macromonomers. The general principles of free radical polymerization methods are well understood. See for example, Odian, "Principles of Polymerization", 3rd edition, John Wiley & Sons, 1991, pp. 198–334. The desired monomers and macromonomers are all placed in a reactor, along with a sufficient amount of a mutual solvent so that when the reaction is complete the viscosity of the reaction is reasonable. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the copolymer by addition of a nonsolvent The copolymer can be further purified, as desired.

As an alternative to a batch reaction, the copolymer can be made by a semi-continuous or continuous process. In the semi-continuous process, two or more additions of monomers or macromonomers are made during the polymerization reaction. This is advantageous when the copolymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction.

Examples of related copolymers and how they are made are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference. Additional grafted polymers are also disclosed in U.S. Pat. Nos. 5,166,276 and 5,480,634, Hayama, et al., issued Nov. 24, 1992 and Jan. 2, 1996, respectively, U.S. Pat. No. 5,061,481, Suzuli et al., issued Oct. 29, 1991; U.S. Pat. No. 5,106,609, Bolich et al., issued Apr. 21, 1992; U.S. Pat. No. 5,100,658, Bolich et al., issued Mar. 31, 1992; U.S. Pat. No. 5,100,657, Ansher-Jackson, et al., issued Mar. 31, 1992; and U.S. Pat. No. 5,104,646, Bolich et al., issued Apr. 14, 1992, all of which are incorporated by reference herein in their entirety.

The copolymer composition is characterized by the amount of each monomer charged to the polymerization reaction vessel, or alternatively used in a continuous or semi-continuous process.

By appropriate selection and combination of the particular monomer units and macromonomer units, and by the choice of specific relative ratios of the units well within the ability of one of ordinary skill in the art, the copolymers can be optimized for various physical properties and for compatibility with other ingredients commonly used in hair care applications.

A Monomer Units

The copolymers of the present invention comprise from about 10% to about 99%, preferably from about 40% to about 80%, and more preferably from about 50% to about 70%, by weight of the hydrophobic copolymer, of A monomer units.

The A monomer unit is selected from copolymerizable hydrophobic monomers or mixtures thereof, preferably ethylenically unsaturated monomers. Either a single type of A monomer unit or combinations of two or more A monomer units can be utilized. The A monomers are selected to meet the requirements of the copolymer. Preferably, the A units are soluble or dispersible in the volatile, hydrophobic solvent component. By "copolymerizable", as used herein, is meant that the A monomer can be reacted with or polymerized with the B monomers or C macromonomers in a polymerization reaction using one or more conventional synthetic techniques, such as ionic, emulsion, dispersion, Ziegler-Natta, free radical, group transfer or step growth polymerization. In the present invention, monomers and macromonomers that are copolymerizable using conventional free radical initiated techniques are preferred. The term "ethylenically unsaturated" is used herein to mean a material that contains at least one polymerizable carbon-carbon double bond, which can be mono-, di-, tri- or tetra-substituted.

Nonlimiting classes of A hydrophobic monomers useful herein include monomers selected from the group consisting of unsaturated carboxylic acid esters of C1–C18 alcohols, unsaturated alcohols (preferably having about 12 to about 30 carbons), unsaturated hydrocarbons, aromatic hydrocarbons containing unsaturated alkyl groups, vinyl esters of carboxylic acids, vinyl ethers, allyl esters of carboyxlic acids, allyl ethers, and mixtures thereof.

Representative examples of hydrophobic monomers include acrylic or methacrylic acid esters of $C_1$–$C_{18}$ alcohols such as methanol, ethanol methoxy ethanol, 1-propanol, 1-butanol, 2-methyl-1-propanol, 1-pentanol, 1-decanol, 2-ethylhexanol, cyclohexanol, and the like; dicyclopentenyl acrylate; 4-biphenyl acrylate, pentachlorophenyl acrylate; 3,5-dimethyladamantyl acrylate; 4-methoxycarbonylphenyl methacrylate, trimethylsilyl methacrylate; styrenes such as methyl styrene; t-butyl styrene, isopropyl sytrene; vinyl esters, such as vinyl acetate, vinyl neononanoate, vinyl pivalate; and vinyl propionate; vinyl chloride; vinyl toluene; allyl vinyl ethers, including isobutyl vinyl ether and s-butyl vinyl ether; allyl chloride, allyl acetate, 1,2-butadiene; 1,3-buatdiene, 1,3-hexadiene, 1,3-cyclohexadiene; bicycloheptadiene; 2,3-dicarboxylmethyl-1,6-hexadiene; ethylene; propylene; isoprene; 1-butene, 2-butene, isobutylene, indene; norbornylene; β-pinene; α-pinene; and mixtures thereof.

Preferred hydrophobic monomers suitable for use as the A monomer units include monomers selected from the group consisting of n-butyl methacrylate, isobutyl methacrylate, t-butyl acrylate, t-butyl methacrylate, 2-ethylhexyl methacrylate, methyl methacrylate, t-butyl styrene and mixtures thereof. More preferred are monomer units selected from the group consisting of t-butyl styrene, t-butyl acrylate, t-butyl methacrylate, 2-ethylhexyl methacrylate and mixtures thereof.

B Monomer Units

The copolymers of the present invention comprise from about 1% to about 40%, preferably from about 5% to about 30%, and more preferably from about 10% to about 25%, by weight of the copolymer, of B monomer units.

The B monomer unit is selected from hydrophilic, copolymerizable monomers, preferably ethylenically unsaturated monomers, comprising at least one monomer copolymerizable with the A monomer unit. Either a single type of B monomer unit or combinations of two or more B monomer units can be utilized. The B monomers are selected to meet the requirements of the copolymer. By "copolymerizable", as used herein, is meant that the B monomer can be reacted with or polymerized with the A monomers or C macromonomers in a polymerization reaction using one or more conventional synthetic techniques, such as ionic, emulsion, dispersion, Ziegler-Natta, free radical, group transfer or step growth polymerization. In the present invention, monomers and macromonomers that are copolymerizable using conventional free radical initiated techniques are preferred. The term "ethylenically unsaturated" is used herein to mean a material that contains at least one polymerizable carbon-carbon double bond, which can be mono-, di-, tri- or tetra-substituted. The B monomer units are selected from hydrophilic monomers wherein at least 1% by weight based on the weight of the copolymer, of the copolymer, comprises hydrophilic monomers having at least one acid functional group. The hydrophilic monomers preferably are selected such that a polymer of these monomers has a Tg or a Tm above about –20° C.

Preferred hydrophilic B monomers are copolymerizable with the A and C monomers, and are selected from the group consisting of unsaturated organic mono- and poly- carboxylic acids, unsaturated (meth)acrylates, unsaturated (meth)acrylamides, unsaturated (meth)acrylate alcohols, unsaturated aminoalkylacrylates, unsaturated organic acid anhydrides, unsaturated esters of organic acid anhydrides, hydrophilic unsaturated vinyl compounds, hydrophilic unsaturated allyl compounds, hydrophilic unsaturated imides, salts of the foregoing compounds, and mixtures thereof.

Representative examples of B monomers include acid functional compounds such as acrylic acid, methacrylic acid, maleic acid, crotonic acid and itaconic acid as well as non-acid functional compounds such as N,N-dimethylacrylamide, dimethylaminoethyl methacrylate, quaternized dimethylaminoethyl methacrylate, methacrylamide, N-t-butyl acrylamide, maleic anhydride and its half esters, acrylamide, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization) and mixtures thereof. More preferred are B monomers selected from the group consisting of acrylic acid, methacrylic acid, N,N-dimethyl-acrylamide, dimethylaminoethyl methacrylate, vinyl pyrrolidone, and mixtures thereof. It is remains critical, however, that at least 1% by weight, based on the weight of the copolymer, comprises B monomers having at least one acid functional group.

C Macromonomer Units

The copolymers of the present invention can comprise from about 0% to about 50%, preferably from about 5% to about 40%, and more preferably from about 15% to about 30%, by weight of the copolymer of C macromonomer units.

The C macromonomer units are hydrophobic macromonomers copolymerizable with the A and B monomers, said C macromonomers preferably having an ethylenically unsaturated moiety. Either a single type of C macromonomer unit or combinations or two or more C macromonomer units can be utilized herein. The C macromonomers are selected to meet the requirements of the copolymer. By "copolymerizable", as used herein, is meant that the C macromonomers can be reacted with or polymerized with the A and B monomers in a polymerization reaction using one or more conventional synthetic techniques, as described above.

C macromonomers that are useful herein contain a polymeric portion and a copolyermizable moiety which is preferably an ethylenically unsaturated moiety. Typically, the preferred C macromonomers are those that are endcapped with the ethylenically unsaturated moiety. By "endcapped" as used herein is meant that the ethylenically unsaturated moiety is at or near a terminal position of the macromonomer.

The C macromonomers can be synthesized utilizing a variety of standard synthetic procedures familiar to the polymer chemist of ordinary skill in the art. Furthermore, these macromonomers can be synthesized starting from commercially available polymers. The C macromonomer has a number average molecular weight from about 1500 to about 50,000, preferably from about 5000 to about 50,000, more preferably from about 5,000 to about 30,000, and most preferably from about 8,000 to about 25,000.

Preferably, the C macromonomer units are selected from the group consisting of polysiloxane macromonomers, polyalkylene macromonomers, and mixtures thereof.

Polysiloxane C macromonomers are exemplified by the general formula:

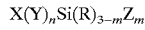

wherein X is an ethylenically unsaturated group copolymerizable with the A monomers, such as a vinyl group; Y is a divalent liking group; R is a hydrogen, hydroxyl, lower alkyl (e.g. $C_1$–$C_4$), phenyl, $C_1$–$C_4$ allyl-substituted aryl, $C_1$–$C_4$ alkoxy, or $C_1$–$C_4$ alkyl or dialkylamino; Z is a monovalent siloxane polymeric moiety having a number average molecular weight of at least about 1500, is essentially unreactive under copolymerization conditions, and is pendant from the vinyl polymeric backbone described above; n is 0 or 1; and m is an integer from 1 to 3.

Preferably, the C macromonomer has a formula selected from the following formulas:

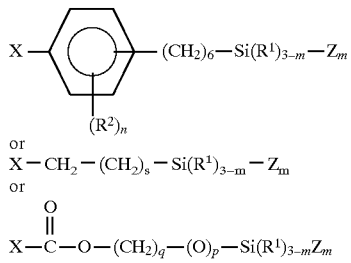

In these structures s is an integer from 0 to 6, preferably 0, 1, or 2, more preferably 0 or 1; m is an integer from 1 to 3, preferably 1; p is 0 or 1; q is an integer from 2 to 6; $R^2$ is selected from the group consisting of $C_1$–$C_{10}$ alkyl or $C_1$–$C_4$ alkyl-substituted aryl, preferably $C_1$–$C_6$ alkyl or $C_1$–$C_4$ alkyl-substituted aryl, more preferably $C_1$–$C_2$ alkyl; n is an integer selected from 0 to 4, preferably 0 or 1, more preferably 0; $R^1$ is hydrogen, hydroxyl, $C_1$–$C_4$ alkyl, $C_1$–$C_4$ alkoxy, $C_1$–$C_4$ alkyl amino or dialkylamino, phenyl, $C_1$–$C_4$ alkyl substituted aryl, preferably $R^1$ is $C_1$–$C_4$ alkyl; X is

$R^3$ is hydrogen or —COOH, preferably $R^3$ is hydrogen; $R^4$ is hydrogen, methyl or —$CH_2COOH$, preferably $R^4$ is methyl; Z is

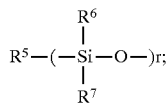

$R^5$, $R^6$, and $R^7$, independently are $C_1$–$C_4$ alkyl, $C_1$–$C_4$ alkoxy, $C_1$–$C_4$ alkyl or dialkylamino, phenyl, $C_1$–$C_4$ allyl-substituted aryl, hydrogen or hydroxyl, preferably $R^5$, $R^6$, and $R^7$ are $C_1$–$C_4$ alkyl; and r is an integer of from about 20 to about 900, preferably about 20 to about 675, more preferably r is from about 100 to about 325. Most preferably, $R^5$, $R^6$, and $R^7$ are methyl, p=0, and q=3.

Polyalkylene macromonomers are exemplified by the general formula:

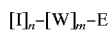

wherein I is an optionally present initiator (i.e. n=0 or 1), W is a hydrophobic monomer unit, E is an endcapping group, and m is an integer from about 10 to about 2000.

I is an optionally present chemical initiator moiety. Without being limited by theory, I can be derived from a chemical initiator or solvent used in the synthesis of the C macromonomer. Nonlimiting examples of such initiators from which I can be derived include hydrogen ion, hydrogen radical, hydride ion, hydroxide ion, hydroxyl radical, peroxide radical, peroxide anion, C1–C20 carbocations, C1–C20 carbanions, C1–C20 carbon radicals, C1–C20 aliphatic and aromatic alkoxy anions, ammonium ion, and substituted ammonium ions (e.g., C1–C20 alkyl and C1–C20 alkoxy substituted), and mixtures thereof. I can be derived from any useful solvent, nonlimiting examples of which include water, methanol, ethanol, propanol, isopropanol, acetone, hexane, dichloromethane, chloroform, benzene, toluene, and mixtures thereof.

W is selected from one or more hydrophobic monomer units. Nonlimiting classes of such monomers include C1–C18 acrylate esters, C1–C18 (alk)acrylate esters, C2–C30 straight and branched chain alkenes, styrenes, C1–C30 vinyl ethers, C4–C30 straight and branched chain dienes, and mixtures thereof.

Nonlimiting examples of W groups include those selected from the group consisting of n-butyl acrylate, dodecyl acrylate, ethyl acrylate, 2-ethybutyl acrylate, n-heptyl acrylate, n-hexylacrylate, iso-butyl acrylate, iso-decyl acrylate, iso-propyl acrylate, 3-methylbutyl acrylate, 2-methylpentyl acrylate, nonyl acrylate, octyl acrylate, 1-propyl acrylate, 2-ethylhexyl methacrylate, octyl methacrylate, n-dodecyl methacrylate, n-octadecyl methacrylate, n-decyl methacrylate, n-pentyl methacrylate, isobutylene, isoprene, 1,2-butadiene, 1,3-butadiene, 5-methyl-1-hexene, 6-methyl-1-heptene, 4,4-dimethyl-1-pentene, iso-butyl vinyl ether, styrene, 2-methyl styrene, 3-methylstyrene, 4-methyl styrene, 2-t-butyl styrene, 3-t-butyl styrene, 4-t-butyl styrene, and mixtures thereof.

E is a copolymerizable moiety or "endcapping" group. Preferably E is an ethylenically unsaturated moiety. More preferred is when E is selected from the group consisting of vinyl, allyl, acryloyl, methacryloyl, ethacryloyl, 2-vinylbenzyl, 3-vinylbenzyl, 4-vinylbenzyl, 2-vinylbenzoyl, 3-vinylbenzoyl, 4-vinylbenzoyl, 1-butenyl, 1-propenyl, isobutenyl, cyclohexenyl, cyclopentenyl, and mixtures thereof. Even more preferred is when E is selected from the group consisting of vinyl, allyl, acryloyl, methacryloyl, ethacryloyl, 3-vinylbenzyl, 4-vinylbenzyl, 3-vinylbenzoyl, 4-vinylbenzoyl, 1-butenyl, 1-propenyl, isobutenyl, and mixtures thereof. Most preferred is when E is selected from the group consisting of vinyl, allyl, acryloyl, methacryloyl, ethacryloyl, 3-vinylbenzyl, 4-vinylbenzyl, and mixtures thereof.

Nonlimiting examples of polysiloxane and polyalkylene C macromonomer units useful herein include those selected from the group consisting of acryloyl, methacryloyl, or 3-, or 4-vinylbenzyl endcapped polymers of polydimethylsiloxane, polydiethylsiloxane, polyphenylmethylsiloxane, polyphenylethylsiloxane, poly (n-butyl acrylate), poly(dodecyl acrylate), poly(2-ethylhexyl acrylate), poly(2-ethylbutyl acrylate), poly(ethyl acrylate), poly(n-heptyl acrylate), poly(n-hexyl acrylate), poly(iso-butyl acrylate), poly(iso-decyl acrylate), poly(iso-propyl acrylate), poly(3-methylbutyl acrylate), poly(2-methylpentyl acrylate), poly(nonyl acrylate), poly(octyl acrylate), poly(propyl acrylate), poly (2-ethylhexyl methacrylate), poly(tridecyl methacrylate), poly (hexyl methacrylate), poly(decyl methacrylate), poly(octyl methacrylate), poly(octadecyl methacrylate), poly(dodecyl methacrylate), poly(n-pentyl methacrylate), poly (isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly (4,4-dimethyl-1-pentene), poly(iso-butyl vinyl ether), poly [4t-butyl vinyl benzene-co-2-ethylhexyl acrylate], poly[2-ethylhexyl acrylate-co-octyl acrylamide), poly[2-ethyl vinyl benzene-co-octyl-methacrylate)], and mixtures thereof.

"Copolymer" type C macromonomers containing two or more different randomly repeating monomer units are useful herein. Nonlimiting examples of these "copolymer type of macromonomers include acryloyl endcapped poly[co(4-t-butyl vinyl benzene)(2,4-dimethyl vinyl benzene)], poly[co (4-t-butyl vinyl benzene)(2-ethylhexyl acrylate)], poly[co(2, 4-dimethyl vinyl benzene)(2-ethylhexyl acrylate)], poly[co (2-ethyl vinyl benzene)(octylmethacrylate)], and the like.

Nonlimiting Examples of Polymers of the Present Invention

Nonlimiting examples of polymers useful for making the complexes of the present invention include those selected from the group consisting of poly[(t-butylacrylate-co-acrylic acid)-graft-poly(dimethylsiloxane)], poly[(4-t-butylstyrene-co-acrylic acid)-graft-poly(dimethylsiloxane)], poly[t-butylacrylate-co-acrylic acid)-graft-poly(isobutylene)], poly[(4-t-butylstyrene-co-acrylic acid)-graft-poly(isobutylene)], poly[(t-butylstyrene-co-acrylic acid)-graft-poly(2-ethylhexyl methacrylate)], poly[(4-t-butylacrylate-co-styrene-co-acrylic acid)-graft-poly(isobutylene)], poly[(t-butylacrylate-co-methacrylic acid)-graft-poly (dimethylsiloxane)], poly[(4-t-butylstyrene-co-methacrylic acid)-graft-poly(dimethylsiloxane)], poly[t-butylacrylate-co-methacrylic acid)-graft-poly(isobutylene)], poly[(4-t-butylstyrene-co-methacrylic acid)-graft-poly(isobutylene)], poly[(t-butylstyrene-co-methacrylic acid)-graft-poly(2-ethylhexyl methacrylate)], poly[(4-t-butylacrylate-co-styrene-co-methacrylic acid)-graft-poly(isobutylene)], and mixtures thereof.

The following more specific nonlimiting examples of polymers useful for making the complexes of the compositions of the present invention include the following. The weight percents refer to the amount of monomer and macromonomer reactants added in the polymerization reaction, not necessarily the amount in the finished polymer.

(I) a copolymer prepared from the polymerization reaction of 10 weight percent acrylic acid, 70 weight percent isobutylmethacrylate and 20 weight percent polydimethylsiloxane macromonomer having a weight average molecular weight of about 20,000.

(II) a copolymer prepared from the polymerization reaction of 20 weight percent acrylic acid, 62 weight percent t-butyl acrylate and 18 weight percent polydimethylsiloxane macromonomer having a weight average molecular weight of about 15,000.

(III) a copolymer prepared from the polymerization reaction of 50 weight percent t-butylacrylate, 10 weight percent t-butyl methacrylate, 10 weight percent acrylic acid, 10 weight percent ethylhexyl methacrylate and 20 weight percent polydimethylsiloxane macromonomer having a weight average molecular weight of about 10,000.

(IV) a copolymer prepared from the polymerization reaction of 60 weight percent t-butylacrylate, 15 weight percent acrylic acid, 10 weight percent ethylhexyl methacrylate and 15 weight percent polydimethylsiloxane macromonomer having a weight average molecular weight of about 10,000.

(V) a copolymer prepared from the polymerization reaction of 70 weight percent t-butylacrylate, 10 weight percent methacrylic acid, and 20 weight percent polyisobutylene macromonomer having a weight average molecular weight of about 10,000.

(VI) a copolymer prepared from the polymerization reaction of 75 weight percent t-butylacrylate, 5 weight percent acrylic acid, and 20 weight percent polydimethylsiloxane macromonomer having a weight average molecular weight of about 10,000.

(VI) a copolymer prepared from the polymerization reaction of 70 weight percent t-butylacrylate, 10 weight percent acrylic acid, and 20 weight percent ethylhexyl methacrylate.

(VII) poly[(t-butyl acrylate-co-acrylic acid)-graft-polydimethylsiloxane)] having a weight average molecular weight of about 700,000, comprising about 67% t-butyl acrylate, about 3% acrylic acid, and about 30% dimethylsiloxane macromonomer with a weight average molecular weight of about 11,000.

Fatty Amine

The copolymer component of the present invention comprises from about 1% to about 65%, preferably from about 10% to about 60%, and more preferably from about 30% to about 50%, based on the weight of the copolymer complex, of a complexing, fatty amine and derivatives thereof and salts thereof.

Fatty amines useful to compositions of the present invention include primary, secondary and tertiary amines, quaternary ammonium salts, alkyl substituted heterocyclic amines, and polyamines such as diamines and triamines. Also useful herein are salts of these amines and quaternized derivatives of these amines.

It is critical to the present invention that copolymer complex formed by the acid functional monomer and the complexing amine be soluble or dispersible in the volatile, hydrophobic solvent component discussed below. Without being limited by theory, it is believed that the fatty amines associate with the acid functional monomers of the copolymer backbone so as to shield the hydrophilic, acid functional group from the hydrophobic solvent, improving the stability of the solubilized and/or dispersed copolymer complex Primary amines or salts thereof having the formula $R^1$—$NH_2$ wherein $R^1$ is a $C_1$–$C_{22}$ straight or branched chain aliphatic, hydroxyalkyl, amidoalkyl, carboxyalkyl, cyclic, alkoxy, polyalkoxy, or hydroxypolyalkoxy group function as useful fatty amines.

Secondary amines or salts thereof having the formula $R^1R^2$—NH wherein $R^1$ and $R^2$ are independently a $C_1$–$C_{22}$ straight or branched chain aliphatic, hydroxyalkyl, amidoalkyl, carboxyalkyl, cyclic, alkoxy, polyalkoxy, or hydroxypolyalkoxy group also function as useful fatty amines.

Additionally, tertiary amines or salts thereof having the formula $R^1R^2R^3N$ wherein $R^1$, $R^2$ and $R^3$ are independently a $C_1$–$C_{22}$ straight or branched chain aliphatic, hydroxyalkyl, amidoalkyl, carboxyalkyl, cyclic, alkoxy, polyalkoxy, or hydroxypolyalkoxy group function well as fatty amines.

Other preferred complexing amines are quaternary ammonium compounds having the formula $R^1R^2R^3R^4N^+$ [$X^-$] wherein $R^1$, $R^2$, $R^3$ and $R^4$ are independently a $C_1$–$C_{22}$ straight or branched chain aliphatic, hydroxyalkyl, amidoalkyl, carboxyalkyl, cyclic, alkoxy, polyalkoxy, or hydroxypolyalkoxy group and X is an anion. Examples of quaternary ammonium complexing amines include $C_{12}$–$C_{18}$ alkyl dimethylammonium chloride, octadecyltrimethylammonium chloride, cetyltrimethylammonium bromide, n-dodecyltrimethylammonium hydroxide, tallow trimonium chloride and n-octadecyltri-n-butylammonium nitrate.

Polyamines or salts thereof are also suitable for use in the present invention. Suitable polyamines are those having the formula $R^1R^2$—$N((CH_3)_xN)_n$—$R^1R^2$ wherein $R^1$ and $R^2$ are independently a hydrogen atom or a $C_1$–$C_{22}$ straight or branched chain aliphatic, hydroxyalkyl, amidoalkyl, carboxyalkyl, cyclic, alkoxy, polyalkoxy or hydroxypolyalkoxy group, x is an integer of 1 to 3, and n is an integer from 1 to 5. Representative polyamines are ethylenediamine, diethylenetriamine triethylenetetraamine, tetraethylenepentamine, pentaethylenehexamine, tallow propylenediamine, 1,2-propanediamine, 1,3,5-pentanetriamine, and ethylenediaminetetraacetic acid (EDTA).

Heterocyclic amines or salts thereof having $C_1$–$C_{22}$ straight or branched chain allyl substituted imidazolines, morpholines, or piperidines are also useful in the present invention. Typical heterocyclic amines include aminoethyl hexadecylimidazoline, N-ethyl morpholine, and N-ethyl piperidine.

Mixtures of the above fatty amines may also be used. Preferred for use in forming the copolymer complexes of the present invention are tertiary amines or salts thereof.

The copolymers of the present invention can be complexed with the fatty amines either during the polymerization process or after the polymerization process as part of a final complexing step preferably at a weight ratio of copolymer to fatty amine of from about 50:1 to about 1:1, more preferably from about 3:1 to about 10:7, more preferably from about 15:7 to about 10:7.

Volatile, Hydrophobic Solvent component

The compositions of the present invention further comprises from about 1% to about 99.75%, preferably from about 4% to about 50%, and more preferably from about 4% to about 20%, based on the weight of the composition, of a volatile, hydrophobic solvent for the copolymer complex.

The term "solvent", as used herein, means a liquid suitable for solubilizing or dispersing one or more of a variety of substances. The term "solvent component" as used herein means a liquid comprised of a single solvent or a mixture of solvents. The term "volatile", as used herein, means that the solvent exhibits a significant vapor pressure at ambient conditions (e.g., 1 atmosphere at 25° C.), as understood by those skilled in the scientific arts. Specially, the solvent component has a boiling point at one atmosphere of about 260° C. or less, preferably about 230° C. or less, more preferably about 215° C. or less, and most preferably about 210° C. or less and a solubility parameter of about 8.5 $(cal/cm^3)^{1/2}$ or less. In addition, the boiling point of the solvent will generally be at least about 50° C., preferably at least about 90° C. The solvent component should also be acceptable for topical application to the hair and the skin. The copolymers composed of the monomer and/or macromer units of the present invention must be soluble or dispersible in the volatile, hydrophobic solvent component once complexed with the fatty amine complexing agent of the present invention.

Hydrophobic solvents suitable for use in the volatile, hydrophobic solvent component are selected from the group consisting of branched chain hydrocarbons, silicones, and mixtures thereof.

Preferred hydrophobic branched chain hydrocarbons useful as the solvent component herein contain from about 7 to about 14, more preferably from about 10 to about 13, and most preferably from about 11 to about 12 carbon atoms. Saturated hydrocarbons are preferred, although it is not intended to exclude unsaturated hydrocarbons. Examples of such preferred branched chain hydrocarbons include isoparaffins of the above chain sizes. Isoparaffins are commercially available form Exxon Chemical Co; examples include Isopar E ($C_8$–$C_9$ isoparaffins), Isopar™ H and K ($C_{11}$–$C_{12}$ isoparaffins), and Isopar™ L ($C_{11}$–$C_{13}$ isoparaffins) or mixtures thereof. Other suitable branched chain hydrocarbons are isododecane and isoundecane. Isododecane is preferred and is commercially available from Presperse, Inc. (South Plainfield, N.J., USA) as Permethyl™ 99A.

Preferred silicones useful as the volatile hydrophobic solvent component include volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane, and mixtures thereof. More preferred among the silicones are cyclomethicones, examples of which include hexamethyl disiloxane, octamethyl cyclo tetrasiloxane and decamethyl cyclopentasiloxane, which are commonly referred to D4 and D5 cyclomethicone, respectively.

Small amounts of hydrophilic solvents such as water, the $C_1$–$C_6$ alcohols, or mixtures thereof may also be incorporated herein so long as the solubility parameter of the volatile, hydrophobic solvent component is about 8.5 $(cal/cm^3)^{1/2}$ or less.

The copolymer complexes of the present invention are soluble or dispensable in the volatile, hydrophobic solvent component at a concentration by weight of about 0.2%, preferably of about 0.5%, and more preferably of about 1%.

In the case of the improved hair styling embodiments, the copolymer complex and the volatile, hydrophobic solvent are preferably mixed such that the copolymer complex/solvent mixture has a viscosity above about 5,000 cps, preferably from about 7,000 cps to about 250,000 cps and more preferably from about 7,000 cps to about 15,000 cps. All viscosities are measured at 25° C. and at a shear rate of 10 sec$^{-1}$ using a Bohlin cone and plate viscometer Model VOR (cone diameter: 30 mm; cone angle: 2.5°) and are expressed in centipoise. Without being limited by theory, it is believed that these higher viscosity embodiments improve polymer deposition efficiency and/or improve the weld morphology of polymer droplets leading to improved hair style and hold.

Carriers

Hair Care and Topical Skin Care Compositions

The copolymers of the present invention can be formulated into a wide variety of product types, including mousses, gels, lotions, creams, ointments, tonics, sprays, aerosols, shampoos, conditioners, rinses, bar soaps, hand and body lotions, facial moisturizers, solid gel sticks, sunscreens, anti-acne preparations, topical analgesics, mascaras, antiperspirants, deodorants and the like. Carriers optionally used to formulate such product types should be immiscible with the volatile hydrophobic solvent component The term "immiscible" as used herein means the volatile, hydrophobic solvent component has a solubility in the carrier of less than 2% by weight, preferably less than 1%, most preferably less than 0.1% such that at least two liquid phases are formed upon combining the volatile, hydrophobic solvent component with the carrier. The optional Carriers and additional components vary with the product type and can be routinely chosen by one skilled in the art. The following is a description of some of these carriers and additional components.

Hair Care Compositions

The hair care compositions of the present invention can comprise a carrier, or a mixture of such carriers, which are suitable for application to the hair. The carriers are preferably present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular copolymer to be used, and whether the product formulated is meant to be left on the surface to which it is applied (e.g., hair spray, mousse, tonic, or gel) or rinsed off after use (e.g., shampoo, conditioner, rinse).

The carriers used herein can include a wide range of components conventionally used in hair care compositions. The carriers can contain a solvent to dissolve or disperse additional copolymers being used, with water, the C1–C6 alcohols, and mixtures thereof being preferred; and water, methanol, ethanol, isopropanol, and mixtures thereof being more preferred. The carriers can also contain a wide variety of additional materials including, but not limited to acetone, hydrocarbons (such as isobutane, hexane, decene), halogenated hydrocarbons (such as Freons), lina-lool, esters (such as ethyl acetate, dibutyl phthalate), and volatile silicon derivatives (especially siloxanes such as phenyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane, cyclomethicone, and dimethicone having for example, a viscosity at 25° C. of about 2.5 centipoise or less), and mixtures thereof. When the hair care composition is a hair spray, tonic, gel, or mousse the preferred solvents include water, ethanol, volatile silicone derivatives, and mixtures thereof. The solvents used in such mixes may be miscible or immiscible with each other. Mousses and aerosol hair sprays can also utilize any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilize an emulsifying agent. Examples of suitable emulsifying agents include nonionic, cationic, anionic surfactants, or mixtures thereof. Fluorosurfactants are especially preferred, particularly if the product is a hair spray composition and most especially if it is a spray composition having relatively low levels of volatile organic solvents, such as alcohols, and relatively high levels of water (e.g., in excess of about 10%, by weight water). If such an emulsifying agent is used, it is preferably present at a level of from about 0.01% to about 7.5% of the composition. The level of propellant can be adjusted as desired but is generally from about 3% to about 30% of mousse compositions and from about 15% to about 70% of the aerosol hair spray compositions.

Suitable spray containers are well known in the art and include conventional, non-aerosol pump sprays i.e., "atomizers," aerosol containers or cans having propellant, as described above, and also pump aerosol containers utilizing compressed air as the propellant Pump aerosol containers are disclosed, for example, in U.S. Pat. Nos. 4,077,441, Mar. 7, 1978, Olofsson and 4,850,577, Jul. 25, 1989, TerStege, both incorporated by reference herein, and also in U.S. Ser. No. 07/839,648, Gosselin, Lund, Sojka, and Lefebvre, filed Feb. 21, 1992, "Consumer Product Package Incorporating A Spray Device Utilizing Large Diameter Bubbles. Pump aerosols hair sprays using compressed air are also currently marketed by The Procter & Gamble Company under their tradename VIDAL SASSOON AIRSPRAY® hair sprays.

Where the hair care compositions are conditioners and rinses, the carrier can include a wide variety of conditioning materials. Where the hair care compositions are shampoos, the carrier can include surfactants, suspending agents, thickeners etc. Various additional components useful in hair care compositions are described in U.S. Pat. No. 5,106,609, to Bolich, Jr. et al., issued Apr. 21, 1992; and U.S. Pat. No. 4,387,090, to Bolich, Jr. issued Jun. 7, 1983; which are incorporated by reference herein. Some of these additional components are described below.

Topical Skin Care Compositions

The topical cosmetic and pharmaceutical compositions of the present invention can comprise a carrier. The carrier should be "cosmetically and/or pharmaceutically acceptable", which means that the carrier is suitable for topical application to the skin, has good aesthetic properties, is compatible with the copolymers of the present invention and any other components, and will not cause any untoward safety or toxicity concerns.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" *Cosmetics & Toiletries*, vol. 105, pp. 122–139 (December1990); "Sun Products Formulary", *Cosmetics & Toiletries*, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers of the skin care compositions preferably comprise from about 50% to about 99% by weight of the compositions of the present invention, more preferably from about 75% to about 99%, and most preferably from about 85% to about 95%.

Preferred cosmetically and/or pharmaceutically acceptable topical carriers include hydro-alcoholic systems and oil-in-water emulsions. When the carrier is a hydro-alcoholic system, the carrier can comprise from about 1% to about 50% of ethanol, isopropanol, or mixtures thereof, and from about 40% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. Additional components useful in formulating these topical compositions are further described below.

Additional Components

A wide variety of additional components can be employed in the hair care and topical skin compositions herein. Non-limiting examples include the following:

Pharmaceutical Actives

The compositions of the present invention, especially the topical skin care compositions, can comprise a safe and effective amount of a pharmaceutical active. The phrase "safe and effective amount", as used herein, means an amount of an active high enough to significantly or positively modify the condition to be treated, but low enough to avoid serious side effects (at a reasonable benefit/risk ratio), within the scope of sound medical judgment. A safe and effective amount of the pharmaceutical active will vary with the specific active, the ability of the composition to penetrate the active through the skin, the amount of composition to be applied, the particular condition being treated, the age and physical condition of the patient being treated, the severity of the condition, the duration of the treatment, the nature of concurrent therapy, and like factors.

The pharmaceutical actives which can be used in the compositions of the present invention preferably comprise from about 0.1% to about 20% by weight of the compositions, more preferably from about 0.1% to about 10%, and most preferably from about 0.1% to about 5%. Mixtures of pharmaceutical actives may also be used.

Nonlimiting examples of pharmaceutical actives can include the following:

Useful pharmaceutical actives in the compositions of the present invention include anti-acne actives. Anti-acne actives preferred for use in the present invention include the keratolytics such as salicylic acid, sulfur, lactic acid, glycolic, pyruvic acid, urea, resorcinol, and N-acetylcysteine; retinoids such as retinoic acid and its derivatives (e.g., cis and trans); antibiotics and antimicrobials such as benzoyl peroxide, octopirox, erytlromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymmol sulfate and its derivatives, deoxycholate, and cholate. Preferred for use herein is salicylic acid.

Useful pharmaceutical actives in the compositions of the present invention include analgesic actives. Analgesic actives suitable for use in the present compositions include salicylic acid derivatives such as methyl-salicylate, species and derivatives of the genus capsicum such as capsaicin and non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Useful pharmaceutical actives in the compositions of the present invention include antipruritic drugs. Antipruritic actives preferred for inclusion in compositions of the present invention include pharmaceutically-acceptable salts of methdilizine and trimeprazine. Useful pharmaceutical actives in the compositions of the present invention include anesthetic actives. Anesthetic actives preferred for inclusion in compositions of the present invention include pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine and phenol. Useful pharmaceutical actives in the compositions of the present invention include antimicrobial actives (antibacterial, antifungal, antiprotozoal and antiviral drugs). Antimicrobial actives preferred for inclusion in compositions of the present invention include pharmaceutically-acceptable salts of b-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole.

Also useful herein are sunscreening agents. A wide variety of sunscreening actives are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Preferred among those sunscreens which are useful in the compositions of the instant invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening actives disclosed therein have, in a single molecule, two distinct chromophore moieties which exhibit different ultra-violet radiation absorption spectra. One of the chromophore moieties absorbs pre-dominantly in the UVB radiation range and the other absorbs strongly in the UVA radiation range. These sunscreening actives provide higher efficacy, broader UV absorption, lower skin penetration and longer lasting efficacy relative to conventional sunscreens. Especially preferred examples of these sunscreens include those selected from the group consisting of 4-N,N-2-ethylhexyl) methylaminobenzoic acid ester of 2,4-dihydroxybenzophenone, 4-N,N-(2-ethylhexyl)

methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Also useful in the present invention are sunless tanning actives including dihydroxyacetone, glyceraldehyde, indoles and their derivatives, and the like. These sunless tanning actives may also be used in combination with the sunscreen agents.

Other useful actives include skin bleaching (or lightening) actives including but not limited to hydroquinone, ascorbic acid, kojic acid and sodium metabisulfite.

Other useful actives which are especially useful for hair care compositions include anti-dandruff actives such as zinc pyrithione, octopirox, selenium disulfide, sulfur, coal tar, and the like.

Other useful actives include antiperspirant actives. Suitable for use herein are those which comprise any compound, composition or mixture thereof having antiperspirant activity. Astringent metallic salts are preferred antiperspirant materials for use herein, particularly the inorganic and organic salts of aluminum, zirconium and zinc, as well as mixtures thereof. Particularly preferred are the aluminum and zirconium salts, such as aluminum halides, aluminum hydroxy halides, zirconyl oxide halides, zirconyl hydroxy halides, and mixtures thereof.

Additionally, deodorant actives in the form of bacteriostats may be incorporated into the present compositions. Suitable deodorant bacteriostats include 2,2'-methylenebis (3,4,6-trichlorophenol), 2,4,4'-trichloro-2'-hydroxy (diphenyl ether), zinc phenolsulfonate, 2,2'-thiobis(4,6-dichlorophenol), p-chloro-m-xylenol, dichloro-m-xylenol and the like. Most preferred is 2,4,4'-trichloro-2'-hydroxy (diphenyl ether), which is generically known as triclosan and available from the Ciba-Geigy Corporation under the trademark, Irgasan DP-300 Registered TM. When triclosan is utilized it will be present in a range from about 0.05 to about 0.9%, preferably from about 0.1 to about 0.5% by weight of the composition. Other types of bacteriostats include sodium N-lauroyl sarcosine, sodium N-palmitoyl sarcosine, lauroyl sarcosine, N-myristoyl glycine, potassium N-lauroyl sarcosine and aluminum chlorhydroxy lactate (sold by Reheis Chemical Company under trademark of Chloracel).

Conditioners

Conditioning agents useful herein, and especially useful for hair care compositions, include hydrocarbons, silicone fluids, and cationic materials.

The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Silicone conditioning agents useful herein can include either cyclic or linear polydimethylsiloxanes, phenyl and alkyl phenyl silicones, and silicone copolyols. The linear volatile silicones generally have viscosities of less than about 5 centistokes at 25° C., while the cyclic materials have viscosities less than about 10 centistokes.

Cationic conditioning agents useful herein include quaternary ammonium salts or the salts of fatty amines. These additional cationic agents are used herein for the purpose of providing conditioning and are separate and apart from the complexing agents of the present invention. Preferred quaternary ammonium salts are dialkyl dimethyl ammonium chlorides, wherein the alkyl groups have from 12 to 22 carbon atoms and are derived from long-chain fatty acids. Representative examples of quaternary ammonium salts include ditallow dimethyl ammonium chloride, ditallow dimethyl ammonium methyl sulfate, dihexadecyl dimethyl ammonium chloride, and di(hydrogenated tallow) ammonium chloride. Other quaternary ammonium salts useful herein are dicationics such as tallow propane diammonium dichloride. Quaternary imidazolinium salts are also useful herein. Examples of such materials are those imidazolinium salts containing C12–C22 alkyl groups such as 1-methyl-1-[(stearoylamide)ethyl]-2-heptadecyl-4,5-dihydroimidazolinium chloride, 1-methyl-1-[(palmitoylamide)ethyl]-2-octadecyl4,5-dihydroimidazolinium chloride and 1-methyl-1-[(tallowamide)-ethyl]-2-tallow-imidazolinium methyl sulfate. Also useful herein are salts of fatty amines. Examples of such compounds include stearylamine hydrochloride, soyamine hydrochloride, and stearylamine formate. Useful conditioning agents are disclosed in U.S. Pat. No. 4,387,090, to Bolich, issued Jun. 7, 1983, which is incorporated by reference herein.

Humectants and Moisturizers

The compositions of the present invention can contain one or more humectant or moisturizing materials. A variety of these materials can be employed and each can be present at a level of from about 0.1% to about 20%, more preferably from about 1% to about 10% and most preferably from about 2% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Preferred humectants and moisturizers are glycerol, butylene glycol, hexylene glycol, and mixtures thereof.

Surfactants

The compositions of the present invention, especially the shampoo and conditioner compositions, can contain one or more surfactants. These surfactants are useful adjuncts for the carriers of the present compositions, and are not required for solubilizing, dispersing or complexing the copolymers of the present invention. For a shampoo, the level is preferably from about 10% to about 30%, preferably from 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants. A wide variety of surfactants useful herein are disclosed in U.S. Pat. No. 5,151,209, to Mc Call et al., issued Sep. 29, 1992; U.S. Pat. No. 5,151,210, to Steuri et al., issued Sep. 29, 1992; and U.S. Pat. No. 5,120,532, to Wells et al., issued Jun. 9, 1992, all of which are incorporated by reference herein.

Nonlimiting examples of these surfactants include anionic surfactants such as alkyl and alkyl ether sulfates. These materials typically have the respective formulae $ROSO_3M$ and $RO(C_2H_4O)_xSO_3M$, wherein R is alkyl or alkenyl of from about 10 to about 20 carbon atoms, x is 1 to 10, and M is a water-soluble cation such as ammonium, sodium, potassium and triethanolamine. Another suitable class of anionic surfactants are the water-soluble salts of the organic, sulfuric acid reaction products of the formula:

$$R_1\text{—}SO_3\text{—}M$$

wherein $R_1$ is chosen from the group consisting of a straight or branched chain, saturated aliphatic hydrocarbon radical having from about 8 to about 24, preferably about 12 to about 18, carbon atoms; and M is a cation. Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Still other anionic synthetic surfactants include the class designated as succinamates, olefin sulfonates having about 12 to about 24 carbon atoms, and b-alkyloxy alkane sulfonates. Many additional nonsoap synthetic anionic surfactants are described in *McCutcheon's, Detergents and Emulsifiers,* 1984 *Annual* published by Allured Publishing Corporation, which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants useful herein are preferably used in combination with an anionic, amphoteric or zwitterionic surfactant. These nonionic surfactants can be broadly defined as compounds produced by the condensation of alkylene oxide groups (hydrophilic in nature) with an organic hydrophobic compound, which may be aliphatic or alkyl aromatic in nature.

Cationic surfactants useful in compositions of the present invention are disclosed in the following documents, all incorporated by reference herein: M.C. Publishing Co., *McCutcheon's, Detergents & Emulsifiers,* (North American edition 1979); Schwartz, et al., *Surface Active Agents, Their Chemistry and Technology,* New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant is present at from about 0.05% to about 5%.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic water-solubilizing group, e.g., carboxy, sulfonate, sulfate, phosphate, or phosphonate. Other zwitterionics such as betaines are also useful in the present invention. Examples of betaines include the high alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl di-methyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine).

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Carboxylic Acid Copolymer Thickeners

Another component useful in the compositions herein is a carboxylic copolymer thickener. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred polymers for use herein are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ allyl, —CN, —COOH and mixtures thereof). The second type of polymer is a crosslinked copolymer having a first monomer selected from the group consisting of an acrylic acid monomer or derivative thereof (as just described in the previous sentence), a short chain alcohol (i.e. a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH—, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaeythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are incorporated by reference herein. See also, *CTFA International Cosmetic Ingredient Dictionary*, fourth edition, 1991, pp. 12 and 80; which are also incorporated herein by reference.

Examples of commercially available homopolymers of the first type useful herein include the carbomers, which are homopolymers of acrylic acid crosslinked with allyl ethers of sucrose or pentaerytritol. The carbomers are available as the Carbopol® 900 series from B. F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Pemulen TR-1, and Pemulen TR-2, from B. F. Goodrich. In other words, examples of carboxylic acid polymer thickeners useful herein are those selected from the group consisting of carbomers, acrylates/C10–C30 alkyl acrylate crosspolymers, and mixtures thereof.

The compositions of the present can comprise from about 0.025% to about 1%, more preferably from about 0.05% to about 0.75% and most preferably from about 0.10% to about 0.50% of the carboxylic acid polymer thickeners.

Emulsifiers

The compositions herein can contain various emulsifiers. These emulsifiers are useful for emulsifying the various carrier components of the compositions herein, and are not required for solubilizing or dispersing the copolymers of the present invention. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5% of the compositions of the present invention.

Emollients

The compositions useful in the methods of the present invention can also optionally comprise at least one emollient. Examples of suitable emollients include, but are not limited to, volatile and non-volatile silicone oils, highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 1% to about 50%, preferably from about 1% to about 25%, and more preferably from about 1% to about 10% by weight of the compositions useful in the present invention.

Additional Components

A variety of additional components can be incorporated into the compositions herein. Nonlimiting examples of these additional components include vitamins and derivatives thereof (e.g., ascorbic acid, vitamin E, tocopheryl acetate, retinoic acid, retinol, retinoids, and the like); low pH thickening agents (e.g. polyacrylamide and $C_{13-14}$ isoparaffin and laureth-7, available as Sepigel from Seppic Corporation; polyquaternium and mineral oil, available as Salcare SC92, from Allied Colloids; crosslinked methyl quaternized dimethylaminomethacrylate and mineral oil, available as Salcare SC95 from Allied Colloids; resins; gums and thickeners such as xanthan gum, carboxymethyl cellulose, hydroxymethyl cellulose, hydroxyethyl cellulose, alkyl-modified hydroxyalkyl celluloses (e.g. long chain allyl modified hydroxyethyl celluloses such as cetyl hydroxyethylcellulose), and magnesium aluminum silicate; cationic polymers and thickeners (e.g., cationic guar gum derivatives such as guar hydroxypropyltrimonium chloride and hydroxypropyl guar hydroxypropyltrimonium chloride, available as the Jaguar C series from Rhone-Poulenc; polymers for aiding the film-forming properties and substantivity of the composition (such as a copolymer of eicosene and vinyl pyrrolidone, an example of which is available from GAF Chemical Corporation as Ganex® V-220); suspending agents such as ethylene glycol distearate and the like; preservatives for maintaining the antimicrobial integrity of the compositions; skin penetration aids such as DMSO, 1-dodecylazacycloheptan-2-one (available as Azone from the Upjohn Co.) and the like; antioxidants; chelators and sequestrants; and aesthetic components such as fragrances, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like.

Method of Using Hair and Skin Care Compositions

The hair care and skin care compositions of the present invention are used in conventional ways to provide the desired benefit appropriate to the product such as hair styling, holding, cleansing, conditioning and the like for hair care compositions and benefits such as moisturization, sun protection, anti-acne, anti-wrinkling, artificial tanning, analgesic, and other cosmetic and pharmaceutical benefits for skin care compositions. Such methods of use depend upon the type of composition employed but generally involve application of an effective amount of the product to the hair or skin, which may then be rinsed from the hair or skin (as in the case of shampoos and some conditioning products) or allowed to remain on the hair (as in the case of spray, mousse, or gel products), or allowed to remain on the skin (as in the case of the skin care compositions). By "effective amount" is meant an amount sufficient to provide the benefit desired. Preferably, hair rinse, mousse, and gel products are applied to wet or damp hair prior to drying and styling of the hair. After such compositions are applied to the hair, the hair is dried and styled in the usual ways of the user. Hair sprays are typically applied to dry hair after it has already been dried and styled. Cosmetic and pharmaceutical topical skin care compositions are applied to and rubbed into the skin.

EXAMPLES

The following examples further illustrate preferred embodiments within the scope of the present invention. The examples are given solely for the purposes of illustration and are not to be construed as limitations of the present invention as many variations of the invention are possible without departing from its spirit and scope.

Ingredients are identified by chemical or CTFA name.

The following synthetic procedure is exemplary of the methods useful for synthesizing the copolymers of the present invention.

Example 1
Synthesis of Poly[(t-butyl acrylate)-(acrylic acid-graft-polydimethylsiloxane)]

Place 60 parts of t-butyl acrylate, 20 parts acrylic acid and 20 parts of polydimethylsiloxane macromonomer (13,000 MW) (commercially available from 3M St. Paul, Minn.) in a flask. Add sufficient acetone as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.5% to about 1.0% by weight relative to the amount of monomer. Heat to 60° C. and maintain this temperature for 6 hours while agitating. Terminate the reaction by cooling to room temperature. The polymer is purified by drying off the reaction solvent in an oven.

Example 2
Synthesis of Poly[(t-butyl acrylate)-(methacrylic acid)-graft-polydimethylsiloxane)]

Place 70 parts of t-butyl acrylate, 10 parts methacrylic acid and 20 parts of polydimethylsiloxane macromonomer (13,000 MW) (commercially available from 3M, St. Paul, Minn.) in a flask. Add sufficient acetone as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.5% to about 1.0% by weight relative to the amount of monomer. Heat to 60° C. and maintain this temperature for 6 hours while agitating. Terminate the reaction by cooling to room temperature. The polymer is purified by drying off the reaction solvent in an oven.

Example 3
Synthesis of Poly[(t-butyl acrylate)-(methacrylic acid )-(2-ethylhexylmethacrylate)]

Place 70 parts of t-butyl acrylate, 10 parts methacrylic acid and 20 parts of 2-ethylhexylmethacrylate in a flask. Add sufficient acetone as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.5% to about 1.0% by weight relative to the amount of monomer. Heat to 60° C. and maintain this temperature for 6 hours while agitating. Terminate the reaction by cooling to room temperature. The polymer is purified by drying off the reaction solvent in an oven.

Example 4
Synthesis of Poly[(t-butyl acrylate)acrylic acid)-graft-polyisobutylene)]

Place 60 parts of t-butyl acrylate, 20 parts acrylic acid and 20 parts of polyisobutylene macromonomer in a flask. Add sufficient acetone as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.5% to about 1.0% by weight relative to the amount of monomer. Heat to 60° C. and maintain this temperature for 6 hours while agitating. Terminate the reaction by cooling to room temperature. The polymer is purified by drying off the reaction solvent in an oven.

Example 5
Synthesis of Poly[(t-butyl acrylate)-(methacrylic acid)-graft-polyisobutylene)]

Place 70 parts of t-butyl acrylate, 10 parts methacrylic acid and 20 parts of polyisobutylene macromonomer in a flask. Add sufficient acetone as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.5% to about 1.0% by weight relative to the amount of monomer. Heat to 60° C. and maintain this temperature for 6 hours while agitating. Terminate the reaction by cooling to room temperature. The polymer is purified by drying off the reaction solvent in an oven.

Example 6
Synthesis of Poly[(t-butyl acrylate)-(methacrylic acid )-(2-ethylhexylmethacrylate)]

Place 70 parts of t-butyl acrylate, 10 parts methacrylic acid and 20 parts of 2-ethylhexylmethacrylate in a flask. Add sufficient acetone as the reaction solvent to produce a final monomer concentration of 20%. Purge the vessel with an inert atmosphere, preferably nitrogen or argon. Add initiator, (2,2'-azobisisobutyronitrile) to a level appropriate for the desired molecular weight. Typically this is in the range of about 0.5% to about 1.0% by weight relative to the amount of monomer. Heat to 60° C. and maintain this temperature for 6 hours while agitating. Terminate the reaction by cooling to room temperature. The polymer is purified by drying off the reaction solvent in an oven.

By varying the monomers and macromonomers used, the general procedures given above in Examples 1–6, is used to prepare other copolymers of the present invention.

Example 7

The following is a hair conditioner composition representative of the present invention.

| Component | Weight % |
|---|---|
| Water | Q.S. to 100% |
| Hydrophobically Modified Hydroxyethylcellulose[1] | 0.25% |
| Stearalkonium Chloride | 0.87% |
| Cetyl Alcohol | 1.85% |
| Stearyl Alcohol | 0.21% |
| Stearamidopropyl Dimethylamine | 0.50% |
| CF1213 ®[2] | 2.33% |
| Methylchloroisothiazolinone Methylisothiazolinone | 0.03% |
| Perfume | 0.33% |
| Copolymer 3[3] | 2.00% |
| Dimethylmyristamine (ARMEEN DM14D)[4] | 0.56% |
| Cyclomethicone D4 | 9.63% |

[1]Polysurf 67 ® supplied by Aqualon
[2]Dimethicone Gum in D5 cyclomethicone; commercially available from GE
[3]Poly[t-butyl acrylate)-(methacrylic acid)-(2-ethylhexylmethacrylate)]
[4]Commercially available from Akzo This product is prepared by dispersing the copolymer in Cyclomethicone D4 (solvent component) then adding the dimethylmyristamine. Heat the solution to 65° C. and use an appropriate homogenizer to facilitate incorporation of the copolymer into the solvent component. The other components (except Kathon and perfume) are mixed in a separate vessel at a temperature high enough (80° C.) to melt the solids. The polymer/solvent component mixture and the CF1213® are added separately to the other components after those have been cooled to at least 45° C. Finally, Kathon and perfume are added, and the product cooled to ambient. This composition is useful for application to the hair to provide conditioning, styling and hold benefits.

Example 8

The following is a hair conditioner composition representative of the present invention.

| Component | Weight % |
|---|---|
| Water | Q.S. to 100% |
| Hydrophobically Modified Hydroxyethylcellulose[1] | 0.50% |
| Stearalkonium Chloride | 0.87% |
| Cetyl Alcohol | 1.85% |
| Stearyl Alcohol | 0.21% |
| Stearamidopropyl Dimethylamine | 0.50% |
| CF1213 ®[2] | 2.33% |
| Methylchloroisothiazolinone Methylisothiazolinone | 0.03% |
| Perfume | 0.33% |
| Copolymer 1[3] | 2.00% |
| dimethyllauramine (ARMEENDM12D)[4] | 1.18% |
| Isododecane | 4.81% |
| Hexamethyl disiloxane | 4.81% |

[1]Polysurf 67 ® supplied by Aqualon
[2]Dimethicone Gum in D5 cyclomethicone; commercially available from GE
[3]Poly[(t-butyl acrylate)-(acrylic acid)-graft polydimethylsiloxane)]
[4]Available from Akzo This product is prepared by dispersing the copolymer in Isododecane and hexamethyl disiloxane (solvent component) then adding the dimethyllauramine. Heat the solution to 65° C. and use an appropriate homogenizer to facilitate incorporation of the copolymer into the solvent component. The other components (except Kathon and perfume) are mixed in a separate vessel at a temperature high enough (80° C.) to melt the solids. The polymer/solvent component mixture and the dimethicone gum are added separately to the other components after those have been cooled to at least 45° C. Finally, Kathon and perfume are added, and the product cooled to ambient. This composition is useful for application to the hair to provide conditioning, styling and hold benefits.

Example 9

The following is a hair shampoo composition representative of the present invention.

| Component | Weight % |
|---|---|
| Water | Q.S. to 100% |
| Ammonium Lauryl Sulfate | 3.14% |
| Ammonium Laureth Sulfate | 13.56% |
| Cetyl Alcohol | 0.45% |
| Stearyl Alcohol | 0.19% |
| Coco Monoethanol Amide | 3.00% |
| Ethylene Glycol Distearate | 2.00% |
| Tricetyl Methyl Ammonium Chloride | 0.50% |
| Methylchloroisothiazolinone Methylisothiazolinone | 0.03% |
| Perfume | 0.20% |
| Copolymer 2[1] | 4.00% |
| Stearamine (ARMEEN 18)[2] | 1.25% |
| Isododecane | 7.40% |

[1]Poly[(t-butyl acrylate)-(methacrylic acid)-graft-polydimethylsiloxane)]
[2]Commercially available from Akzo This product is prepared by dispersing the copolymer in isododecane (solvent component) then adding the stearamine. Heat the solution to 65° C. and use an appropriate homogenizer to facilitate incorporation of the copolymer into the solvent component. The other components are mixed in a separate vessel at a temperature high enough to melt the solids. The polymer/solvent component mixture is added to the other components after those have been cooled. This composition is useful for application to the hair to provide cleansing, styling and hold benefits.

Example 10

The following is a hair shampoo composition representative of the present invention.

| Component | Weight % |
|---|---|
| Water | Q.S. to 100% |
| Cocoamidopropyl Betaine | 8.30% |
| Ammonium Lauryl Sulfate | 2.12% |
| Ammonium Laureth Sulfate | 6.35% |
| Coco Monoethanol Amide | 1.50% |
| Hydroxypropyl Methocellulose (K15) | 0.25% |
| Ethylene Glycol Distearate | 1.50% |
| Tricetyl Methyl Ammonium Chloride | 0.50% |
| Methylchloroisothiazolinone Methylisothiazolinone | 0.03% |
| Perfume | 0.20% |
| Copolymer 4[1] | 3.00% |
| dimethylstearamine (ARMEEN DM18D)[2] | 2.48% |
| Isododecane | 5.00% |
| Cyclomethicone | 5.00% |

[1]Poly[(t-butyl acrylate)-(acrylic acid)-grift-polyisobutylene)]
[2]Commercially available from Akzo This product is prepared by dispersing the copolymer in isododecane and cyclomethicone (solvent component) then adding the dimethylstearamine. Heat the solution to 65° C. and use an appropriate homogenizer to facilitate incorporation of the copolymer into the solvent component. The other components are mixed in a separate vessel at a temperature high enough to melt the solids. The polymer/solvent component solution is added to the other components after those have been cooled.

Example 11

The following is a hair styling gel composition representative of the present invention.

| Component | Weight % |
|---|---|
| Polymer-Solvent component Mix | |
| Copolymer 5[1] | 1.25% |
| dimethylpalmitamine | 0.39% |
| Isopar H ®[2] | 3.75% |
| Premix | |
| Water | 43.00% |
| Hydrogenated Ditallowdimonium Chloride (Quaternium 18) | 1.00% |
| Main Mix | |
| Water | 48.47% |
| Carbopol 940 ® | 0.75% |
| Triethanol Amine | 1.00% |
| Panthenol | 0.05% |
| Perfume | 0.20% |

[1]Poly[(t-butyl acrylate)-(methacrylic acid)-graft-polyisobutylene)]
[2]$C_{11}$–$C_{12}$ Isoparaffin, available from Exxon Chemical Co.

This product is prepared by dispersing the copolymer in Isopar H® (solvent component) then adding the dimethylpalmitamie. Heat the solution to 65° C. and use an appropriate homogenizer to facilitate incorporation of the copolymer into the solvent component. Quaternium 18 is mixed with water at 80° C. The polymer-solvent component mixture is added to the Quaternium 18 containing premix at either high or low temperature. The other components are mixed in a separate vessel at ambient temperature. The Quaternium 18 premix with the polymer/solvent component mixture is cooled (if needed) and added to the other components. This composition is useful for application to the hair to provide conditioning, styling and hold benefits.

Example 12

The following is a spray-on gel hair composition representative of the present invention.

| Component | Weight % |
|---|---|
| Water | Q.S. to 100% |
| Tallowtrimonium Chloride | 0.10% |
| Hydrogenated Ditallowdimonium Chloride (Quaternium 18) | 0.90% |
| Panthenol | 0.05% |
| Perfume | 0.20% |
| Copolymer 6[1] | 1.00% |
| myristamine | 0.25% |
| Hexamethyl disiloxane | 3.00% |

[1]Poly[(t-butyl acrylate)-(methacrylic acid)-(2-ethylhexylmethacrylate)]

This product is prepared by dissolving the copolymer in hexamethyl disiloxane (solvent component) then adding the myristamine. Heat the solution to 65° C. and use an appropriate homogenizer to facilitate incorporation of the copolymer into the solvent component. The other components are mixed in a separate vessel at a temperature high enough (70° C.) to melt the solids. The polymer/solvent component solution is added to the other components at either high or low temperature. This composition is useful for application to the hair to provide conditioning, styling and hold benefits.

Example 13

The following is a hair styling rinse composition representative of the present invention.

| Component | Weight % |
|---|---|
| Premix A | |
| Water | 8.14% |
| Ditallowdimonium Chloride (Varisoft 470) | 1.43% |
| CF1213 ®[1] | 2.33% |
| Amodimethicone | 0.10% |
| Premix B | |
| Water | 5.45% |
| Stearalkonium Chloride | 0.30% |
| Panthenol DL | 0.225% |
| Pantyl Ethyl Ether | 0.025% |
| Main Mix | |
| Water | 66.02% |
| Hydrophobically Modified Hydroxyethylcellulose[2] | 1.23% |
| Xanthan Gum | 0.25% |
| Citric Acid | 0.02% |
| Sodium Citrate | 0.09% |
| Cetyl Alcohol | 0.12% |
| Stearyl Alcohol | 0.08% |
| Polymer-Solvent component Mixture | |
| Copolymer 1[3] | 2.00% |
| Cyclomethicone D4 | 5.00% |
| Hexamethyl disiloxane | 5.00% |
| Dimethylmyristamine (ARMEENDM14D)[4] | 1.33% |
| Methylchloroisothiazolinone Methylisothiazolinone | 0.03% |
| Perfume | 0.33% |
| Benzyl Alcohol | 0.50% |

[1]Dimethicone Gum in D5 cyclomethicone; commercially available from GE
[2]Polysurf 67 ® supplied by Aqualon
[3]Poly[(t-butyl acrylate)-(acrylic acid)-graft-polydimethylsiloxane)]
[4]Commercially available from Akzo This product is prepared by dispersing the copolymer in the cyclomethicone D4 and hexamethyl disiloxane (solvent component) then adding the dimethylmyristamine. Heat the solution to 65° C. and use an appropriate homogenizer to facilitate incorporation of the copolymer into the solvent component. Premixes A and B are prepared by combining materials at 70° C. Premix A goes through a colloid mill and is cooled to 38° C. Materials in 'Main Mix', except benzyl alcohol, are mixed at 65° C. The polymer solution is then added to the 'Main Mix'. Main mix goes through a colloid mill and is cooled to 38° C. Premixes and kin Mix are combined at 38° C. Then the benzyl alcohol is added. This composition is useful for application to the hair to provide conditioning, styling and hold benefits.

Example 14

The following is a hair styling mousse composition representative of the present invention.

| Component | Weight % |
|---|---|
| Water | Q.S. to 100% |
| Tallowtrimonium Chloride | 0.10% |
| Hydrogenated Ditallowdimonium Chloride (Quaternium 18) | 0.90% |
| Lauramine Oxide | 0.20% |
| Panthenol | 0.05% |
| Perfume | 0.20% |
| Copolymer 1[1] | 1.00% |
| lauramine | 0.51% |
| Hexamethyl disiloxane | 3.00% |
| Isobutane | 7.00% |

[1]Poly[(t-butyl acrylate)-(acrylic acid)-graft-polydiethylsiloxane)]

This product is prepared by dispersing the copolymer in hexamethyl disiloxane (solvent component) then adding the lauramine. Heat the solution to 65° C. and use an appropriate homogenizer to facilitate incorporation of the copolymer into the solvent component. The other components (except isobutane) are mixed in a separate vessel at a temperature high enough (70° C.) to melt the solids. The polymer/solvent component solution is added to the other components after those have been cooled. Aluminum aerosol cans are then filled with 93 parts of this batch, affixed with a valve which is crimped into position, and lastly pressure filled with 7 parts Isobutane. This composition is useful for application to the hair to provide conditioning, styling and hold benefits.

Example 15

The following is a hair styling spray composition representative of the present invention.

| Component | Weight % |
|---|---|
| Water | Q.S. to 100% |
| Panthenol | 0.05% |
| Perfume | 0.20% |
| Copolymer 4[1] | 2.00% |
| Dimethylmyristamine | 1.33% |
| Cyclomethicone D4 | 7.00% |
| Isobutane | 25.00% |

[1]poly[(t-butyl acrylate)-(acrylic acid)-graft-polyisobutylene)]

This product is prepared by dispersing the copolymer in Cyclomethicone D4 (solvent component) then adding the dimethylmyristamine. Heat the solution to 65° C. and use an appropriate homogenizer to facilitate incorporation of the copolymer into the solvent component. The other components (except isobutane) are mixed in a separate vessel. The polymer/solvent component solution is added to the other components. Aluminum aerosol cans are then filled with 75 parts of this batch, affixed with a valve which is crimped into position, and lastly pressure filled with 25 parts Isobutane. This composition is useful for application to the hair to provide conditioning, styling and hold benefits When the compositions defined in Examples 4–12 are applied to hair in the conventional manner, they provide effective hair conditioning and styling/hold benefits without leaving the hair with a sticky/stiff feel.

Example 16

The following is a hair styling rinse composition representative of the present invention.

| Component | Weight % |
|---|---|
| Premix A | |
| Water | 8.14% |
| Ditallowdimonium Chloride (Varisoft 470) | 1.43% |
| CF1213 ® (Dimethicone Gum)[2] | 2.33% |
| Amodimethicone | 0.10% |
| Premix B | |
| Water | 5.45% |
| Stearalkonium Chloride | 0.30% |
| Panthenol DL | 0.225% |
| Pantyl Ethyl Ether | 0.025% |
| Main Mix | |
| Water | 71.35% |
| Hydrophobically Modified Hydroxyethylcellulose[1] | 1.23% |
| Xanthan Gum | 0.25% |
| Citric Acid | 0.02% |
| Sodium Citrate | 0.09% |
| Cetyl Alcohol | 0.12% |
| Stearyl Alcohol | 0.08% |
| Polymer-Solvent Mixture | |
| Copolymer #1 | 2.00% |
| Cyclomethicone D4 | 4.67% |
| Dimethylmyristamine (ARMEENDM14D) | 1.33% |
| Methylchloroisothiazolinone Methylisothiazolinone | 0.03% |
| Perfume | 0.33% |
| Benzyl Alcohol | 0.50% |

[1]Polysurf 67 ® supplied by Aqualon
[2]Commercially available from GE

This product is prepared by dispersing the copolymer #1 in the cyclomethicone D4(solvent) then adding the dimethylmyristamine. Heat the solution to 65 C. and use an appropriate homogenizer to facilitate incorporation of the copolymer into the solvent. Premixes A and B are prepared by combining materials at 70° C. Premix A goes through a colloid mill and is cooled to 38° C. Materials in 'Main Mix', except benzyl alcohol, are mixed at 65° C. The polymer solution is then added to the 'Main Mix'. Main mix goes through a colloid mill and is cooled to 38° C. Premixes and Main Mix are combined at 38° C. Then the benzyl alcohol is added. This composition is useful for application to the hair to provide conditioning, styling and hold benefits.

Example 17

The following is a hair styling rinse composition representative of the present invention.

| Component | Weight % |
|---|---|
| Premix A | |
| Water | 8.14% |
| Ditallowdimonium Chloride (Varisoft 470) | 1.43% |
| CF1213 ® (Dimethicone Gum)[2] | 2.33% |
| Amodimethicone | 0.10% |
| Premix B | |
| Water | 5.45% |
| Stearalkonium Chloride | 0.30% |
| Panthenol DL | 0.225% |
| Pantyl Ethyl Ether | 0.025% |
| Main Mix | |
| Water | 70.46% |
| Hydrophobically Modified Hydroxyethylcellulose[1] | 1.23% |
| Xanthan Gum | 0.25% |
| Citric Acid | 0.02% |
| Sodium Citrate | 0.09% |
| Cetyl Alcohol | 0.12% |
| Stearyl Alcohol | 0.08% |
| Polymer-Solvent Mixture | |
| Copolymer #1 | 2.00% |
| Cyclomethicone D4 | 5.56% |
| Dimethylmyristamine (ARMEENDM14D) | 1.33% |
| Methylchloroisothiazolinone Methylisothiazolinone | 0.03% |
| Perfume | 0.33% |
| Benzyl Alcohol | 0.50% |

[1]Polysurf 67 ® supplied by Aqualon
[2]Commercially available from GE

This product is prepared by dispersing the copolymer #1 in the cyclomethicone D4(solvent) then adding the dimethylmyristamine. Heat the solution to 65 C. and use an appropriate homogenizer to facilitate incorporation of the copolymer into the solvent. Premixes A and B are prepared by combining materials at 70° C. Premix A goes through a colloid mill and is cooled to 38° C. Materials in 'Main Mix', except benzyl alcohol, are mixed at 65° C. The polymer solution is then added to the 'Main Mix'. Main mix goes through a colloid mill and is cooled to 38° C. Premixes and 'Main Mix' are combined at 38° C. Then the benzyl alcohol is added. This composition is useful for application to the hair to provide conditioning, styling and hold benefits.

Example 18

The following is a hair styling rinse composition representative of the present invention.

| Component | Weight % |
|---|---|
| Premix A | |
| Water | 8.14% |
| Ditallowdimonium Chloride (Varisoft 470) | 1.43% |
| CF1213 ® (Dimethicone Gum)[2] | 2.33% |
| Amodimethicone | 0.10% |
| Premix B | |
| Water | 5.45% |
| Stearalkonium Chloride | 0.30% |
| Panthenol DL | 0.225% |
| Pantyl Ethyl Ether | 0.025% |
| Main Mix | |
| Water | 72.08% |
| Hydrophobically Modified Hydroxyethylcellulose[1] | 1.23% |
| Xanthan Gum | 0.25% |
| Citric Acid | 0.02% |
| Sodium Citrate | 0.09% |
| Cetyl Alcohol | 0.12% |
| Stearyl Alcohol | 0.08% |
| Polymer-Solvent Mixture | |
| Copolymer #1 | 2.00% |
| Isododecane | 4.09% |
| Dimethyllauramine (ARMEENDM12D) | 1.18% |
| Methylchloroisothiazolinone Methylisothiazolinone | 0.03% |
| Perfume | 0.33% |
| Benzyl Alcohol | 0.50% |

[1]Polysurf 67 ® supplied by Aqualon
[2]Commercially available from GE

This product is prepared by dispersing the copolymer #1 in the cyclomethicone D4(solvent) then adding the dimethylmyristamine. Heat the solution to 65 C. and use an appropriate homogenizer to facilitate incorporation of the copolymer into the solvent. Premixes A and B are prepared by combining materials at 70° C. Premix A goes through a colloid mill and is cooled to 38° C. Materials in 'Main Mix', except benzyl alcohol, are mixed at 65° C. The polymer solution is then added to the 'Main Mix'. Main mix goes through a colloid mill and is cooled to 38° C. Premixes and kin Mix are combined at 38° C. Then the benzyl alcohol is added. This composition is useful for application to the hair to provide conditioning, styling and hold benefits.

Example 19

The following is a sunscreen composition representative of the present invention.

An oil-in-water emulsion is prepared by combining the following components utilizing conventional mixing techniques.

| Ingredients | Weight % |
|---|---|
| Phase A | |
| Water | QS100 |
| Carbomer 954[1] | 0.24 |
| Carbomer 1342[2] | 0.16 |
| Disodium EDTA | 0.05 |
| Phase B | |
| Isoarachidyl Neopentanoate[3] | 2.00 |
| PVP Eicosene Copolymer[4] | 2.00 |
| Octyl Methoxycinnamate | 7.50 |
| Octocrylene | 4.00 |
| Oxybenzone | 1.00 |
| Titanium Dioxide | 2.00 |
| Cetyl Palmitate | 0.75 |
| Stearoxytrimethylsilane (and) Stearyl Alcohol[5] | 0.50 |
| Glyceryl Tribehenate | 0.75 |
| Dimethicone | 1.00 |
| Tocopheryl Acetate | 0.10 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate[6] | 0.25 |
| dL Panthenol | 1.00 |
| Phase E | |
| Cyclomethicone D4 | 4.00 |
| Copolymer 6[7] | 1.00 |
| stearamine | 1.25 |

[1]Available as Carbopol ® 954 from B.F. Goodrich.
[2]Available as Carbopol ® 1342 from B.F. Goodrich.
[3]Available as Ganex V-220 from GAF Corporation.
[4]Available as DC 580 Wax from Dow Corning.
[5]Available as Synchrowax HRC from Croda.
[6]Available as Glydant Plus from Lonza.
[7]Poly[(t-butyl acrylate)-(methacrylic acid)-(2-ethylhexylmethacrylate)]

In a suitable vessel the Phase A ingredients are dispersed in the water and heated to 75°–85° C. In a separate vessel the Phase B ingredients (except DEA-Cetyl Phosphate) are combined and heated to 85°–90° C. until melted. Next, the DEA-Cetyl Phosphate is added to the liquid Phase B and stirred until dissolved. This mixture is then added to Phase A to form the emulsion. The Phase C ingredients are combined until dissolved and then added to the emulsion. The emulsion is then cooled to 40°–45° C. with continued mixing. In another vessel, the Phase D ingredients are heated with mixing to 40°–45° C. until a clear solution is formed and this solution is then added to the emulsion. The emulsion is cooled to 35° C. The Phase E ingredients are combined at 65° C., use an appropriate homogenizer to facilitate incorporation of the copolymer into the solvent component. Phase E is the cooled to 35° C., added and mixed.

This emulsion is useful for topical application to the skin to provide protection from the harmful effects of ultraviolet radiation.

Example 20

The following is a facial moisturizing composition representative of the present invention.

A leave-on facial emulsion composition containing a cationic hydrophobic surfactant is prepared by combining the following components utilizing conventional mixing techniques.

| Ingredient | Weight % |
|---|---|
| Phase A | |
| Water | QS100 |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Octyldodecyl Myristate | 0.30 |
| Potassium Hydroxide | 0.20 |
| Carbomer 1342 | 0.125 |
| Tetrasodium EDTA | 0.10 |
| DMDM Hydantoin and Iodopropynyl Butyl Carbamate | 0.10 |
| Carbomer 951 | 0.075 |
| Phase B | |
| Isododecane | 4.00 |
| Copolymer 2[1] | 1.00 |
| stearamine | 0.31 |

[1]Poly[(t-butyl acrylate)-(methacrylic acid)-graft-polydimethylsiloxane)]

In a suitable vessel the Phase A ingredients are combined to form an emulsion. Phase B is prepared by dispersing the copolymer in Isododecane (solvent component) then adding the stearamine. Heat the solution to 65° C. and use an appropriate homogenizer to facilitate incorporation of the copolymer into the solvent component Cool the Phase B and mix into Phase A using conventional mixing techniques.

This emulsion is useful for application to the skin as a moisturizer.

Example 21

The following is an antiperspirant composition representative of the present invention.

| Component | Weight % |
|---|---|
| PPG 2 Myristyl Propionate | 34.00% |
| Glyceryl $C_{18}$–$C_{36}$ Wax Acid Ester | 0.40% |
| Cyclomethicone | 32.75% |
| Copolymer 1[1] | 1.00% |
| Dimethylmyristamine | 0.67% |
| Aluminum Chlorohydrate | 19.00% |
| PPG 5 Ceteth 20 | 7.50% |
| Water | 1.50% |

[1]Poly(t-butyl acrylate)-(acrylic acid)-graft-polydimethylsiloxane)]

Mix PPG 2 Myristyl Propionate and Glyceryl $C_{18}$–$C_{36}$ Wax Acid Ester, heat to 75° C. Disperse the Chlorohydrate. Disperse the copolymer in Cyclomethicone (solvent component) then add the dimethylmyristamine. Heat the solution to 65° C. and use an appropriate homogenizer to facilitate incorporation of the copolymer into the solvent component. Add the cyclomethicone mixture to the Chlorohydrate dispersion. Mix PPG 5 Ceteth 20 and the water, the add to oils, perfume and cool.

Example 22

The following is an anti-acne composition representative of the present invention.

| Component | Weight % |
|---|---|
| Copolymer-Solvent component Mix | |
| Copolymer 5[1] | 1.00% |
| dimethylpalmitamine | 0.31% |
| Isopar H ®[2] | 3.75% |
| Main Mix | |
| Water | Q.S. to 100% |
| Ethanol (SDA 40) | 40.00% |
| Carbopol 940 ® | 0.75% |
| Triethanol Amine | 1.00% |
| Salicylic Acid | 2.00% |

[1]Poly[(t-butyl acrylate)-(methacrylic acid)-graft-polyisobutylene)]
[2]$C_{11}$–$C_{12}$ Isoparaffin, available from Exxon Chemical Co.

This product is prepared by dispersing the copolymer in Isopar H® (solvent component) then adding the dimethylpalmitamine. Heat the solution to 65° C. and use an appropriate homogenizer to facilitate incorporation of the copolymer into the solvent component. The other components are mixed in a separate vessel at ambient temperature. The copolymer-solvent component premix is cooled (if needed) and added to the other components. This composition is useful for application to the skin to provide improve water resistance and is useful in the treatment of acne.

Example 23

The following is a topical analgesic composition representative of the present invention.

| Component | Weight % |
|---|---|
| Copolymer-Solvent component Mix | |
| Copolymer 1[1] | 1.00% |
| dimethylpalmitamine | 0.74% |
| Isopar H ®[2] | 3.75% |
| Main Mix | |
| Water | Q.S. to 100% |
| Ethanol (SDA 40) | 20.00% |
| Carbopol 940 ® | 0.75% |
| Triethanol Amine | 1.00% |
| Ibuprofen | 2.00% |

[1]Poly[(t-butyl acrylate)-(acrylic acid)-graft-polydimethylsiloxane)]
[2]$C_{11}$–$C_{12}$ Isoparaffin, available from Exxon Chemical Co.

This product is prepared by dispersing the copolymer in Isopar H® (solvent component) then adding the dimethylpalmitamine. Heat the solution to 65° C. and use an appropriate homogenizer to facilitate incorporation of the copolymer into the solvent component. The other components are mixed in a separate vessel at ambient temperature. The copolymer-solvent component premix is cooled (if needed) and added to the other components. This composition is useful for application to the skin to provide improve water resistance and is useful for the analgesic effects.

What is claimed is:
1. A personal care composition, comprising:
   A.) a copolymer complex comprising:
      a.) a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:

i) from about 10% to about 99% by weight of the copolymer of one or more hydrophobic A monomer units selected from the group consisting of t-butyl acrylate, t-butyl methacrylate, t-butyl styrene, 2-ethylhexyl methacrylate and mixtures thereof, wherein the A monomer units are copolymerizable with the B monomer and C macromonomer units;

ii) from about 1% to about 40% by weight of the copolymer of one or more hydrophilic B monomer units selected from the group consisting of acrylic acid, methacrylic acid, N,N-dimethyl acrylamide, t-butyl acrylamide, vinyl pyrrolidone, and mixtures thereof, wherein the B monomer units are copolymerizable with the A monomer and C macromonomer units and iii) from about 5% to about 40% by weight of the copolymer of one or more C macromonomer units selected from the group of polymers consisting of poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate, poly(iso-propyl acrylate), poly(3-methylbutyl acrylate), poly(2-methylpentyl acrylate), poly(nonyl acrylate), poly (octyl acrylate), poly(propyl acrylate), poly (2-ethylhexyl methacrylate), poly(tridecyl methacrylate), poly (hexyl methacrylate), poly (decyl methacrylate), poly(octyl methacrylate), poly(octadecyl methacrylate), poly(dodecyl methacrylate), poly(n-pentyl methacrylate), poly (isobutylene), poly(isoprene), hydrogenated poly (1,2-butadiene), hydrogenated poly(1,4-butadiene), hydrogenated poly(isoprene), poly(1, 2-butadiene), poly(1-butene), poly(5-methyl-1-hexene), poly(6-methyl-1-heptene), poly(4,4-dimethyl-1-pentene), poly(iso-butyl vinyl ether), poly(4-t-butyl vinyl benzene-co-2-ethylhexyl acrylate), poly(2-ethylhexyl acrylate-co-octyl acrylamide), poly(2-ethyl vinyl benzene-co-octyl methacrylate), and mixtures thereof wherein the polymers are endcapped by an endcapping group selected from the group consisting of acryloyl, methacryloyl, 2-vinylbenzyl, 3-vinylbenzyl, and 4-vinylbenzyl, wherein the C units are hydrophobic macromonomer units, copolymerizable with the A monomer units and the B monomer units, the C macromonomer units having a number average molecular weight of from about 1,500 to about 50,000; and b.) a complexing fatty amine wherein the fatty amine is selected from the group consisting of $C_1$–$C_{22}$ primary amines, $C_1$–$C_{22}$ secondary amines and $C_1$–$C_{22}$ tertiary amines, $C_1$–$C_{22}$ quaternary ammonium salts, $C_1$–$C_{22}$ polyamines, alkyl substituted heterocyclic amines selected from the group consisting of aminoethyl hexadecylimidazoline, N-ethyl morpholine, and N-ethyl piperidine and mixtures thereof, salts thereof and mixtures thereof and wherein the fatty amine forms a complex with the acid functional B monomer units wherein the weight ratio of the copolymer to the fatty amine is from about 50:1 to about 1:1; and B.) a volatile, hydrophobic solvent component for the copolymer complex having a boiling point at 1 atmosphere of about 260° C. or less and a solubility parameter of about 8.5 $(cal/cm^3)^{1/2}$ or less wherein the copolymer complex is soluble or dispersible in the volatile, hydrophobic solvent component.

2. A personal care composition according to claim 1, wherein the complexing fatty amine is a tertiary amine or salt thereof having the formula $R^1R^2R^3N$ wherein $R^1$, $R^2$ and $R^3$ are independently selected from the group consisting of $C_1$–$C_{22}$ straight chain aliphatic, $C_2$–$C_{22}$ hydroxyalkyl, $C_2$–$C_{22}$ amidoalkyl, $C_2$–$C_{22}$ carboxyalkyl, $C_3$–$C_{22}$ cyclic, $C_2$–$C_{22}$ alkoxy, $C_2$–$C_{22}$ polyalkoxy, and $C_2$–$C_{22}$ hydroxypolyalkoxy groups and $C_1$–$C_{22}$ branched chained aliphatic, $C_2$–$C_{22}$ hydroxyalkyl, $C_2$–$C_{22}$ amidoalkyl, $C_2$–$C_{22}$ carboxyalkyl, $C_3$–$C_{22}$ cyclic, $C_2$–$C_{22}$ alkoxy, $C_2$–$C_{22}$ polyalkoxy, and $C_2$–$C_{22}$ hydroxypolyalkoxy groups and mixtures thereof.

3. A personal care composition according to claim 1, wherein the complexing fatty amine is a tertiary amine or salt thereof having the formula $R^1R^2R^3N$ wherein $R^1$ is selected from the group consisting of $C_{10}$–$C_{18}$ straight chain aliphatic, $C_{10}$–$C_{18}$ hydroxyalkyl, $C_{10}$–$C_{18}$ amidoalkyl, $C_{10}$–$C_{18}$ carboxyalkyl, $C_{10}$–$C_{18}$ cyclic, $C_{10}$–$C_{18}$ alkoxy, $C_{10}$–$C_{18}$ polyalkoxy, $C_{10}$–$C_{18}$ hydroxypolyalkoxy groups $C_{10}$–$C_{18}$ branched chained aliphatic, $C_{10}$–$C_{18}$ hydroxyalkyl, $C_{10}$–$C_{18}$ amidoalkyl, $C_{10}$–$C_{18}$ carboxyalkyl, $C_{10}$–$C_{18}$ cyclic, $C_{10}$–$C_{18}$ alkoxy, $C_{10}$–$C_{18}$ polyalkoxy, and $C_{10}$–$C_{18}$ hydroxypolyalkoxy groups provided $R^2$ is a methyl group and $R^3=R^2$.

4. A personal care composition according to claim 3, wherein the copolymer of the copolymer complex is prepared by the polymerization combination of the following relative weight percentages of said A, B and C units:

a. from about 40% to about 80% of said hydrophobic A unit;
   b. from 5% to about 30% of said hydrophilic B unit; and
   c. from about 5% to about 40% of said hydrophobic C unit wherein said C unit has a number average molecular weight of from about 5,000 to about 30,000.

5. A personal care composition according to claim 4, wherein said volatile, hydrophobic solvent component is selected from the group consisting of hydrophobic, volatile $C_7$–$C_{14}$ branched hydrocarbons, hydrophobic, volatile silicones and mixtures thereof.

6. A personal care composition according to claim 5, wherein said volatile, hydrophobic solvent component is selected from the group consisting of hexamethyl disiloxane, isododecane, cyclomethicone and mixtures thereof.

7. A personal care composition according to claim 6, further comprising a carrier selected from the group consisting of mousses, gels, lotions, creams, ointments, tonics, sprays, aerosols, shampoos, conditioners, rinses, bar soaps, hand lotions body lotions, facial moisturizers, and solid gel sticks.

8. A personal care composition according to claim 7, wherein said composition further comprising from about 10% to about 30% by weight of the composition of a synthetic surfactant.

9. A personal care composition according to claim 8, wherein said synthetic surfactant is selected from the group consisting of alkyl sulfates, ethoxylated alkyl sulfates, and mixtures thereof.

10. A personal care composition according to claim 9, wherein the composition is a shampoo.

11. A personal care composition according to claim 7, wherein said composition further comprises a pharmaceutical active selected from the group consisting of antiacne actives, analgesic actives, antipruritic actives, anesthetic actives, antimicrobial actives, sunscreen actives, sunless tanning actives, skin-bleaching actives, anti-dandruff actives, antiperspirant actives, deodorant actives and mixtures thereof.

12. A personal care composition, comprising:
A.) a copolymer complex comprising:
   a.) a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:
      i) from about 10% to about 99% by weight of the copolymer of one or more hydrophobic A monomer units selected from the group consisting of t-butyl acrylate, t-butyl methacrylate, t-butyl styrene, 2-ethylhexyl methacrylate and mixtures thereof, wherein the A monomer units are copolymerizable with the B monomer and C macromonomer units;
      ii) from about 1% to about 40% by weight of the copolymer of one or more hydrophilic B monomer units selected from the group consisting of acrylic acid, methacrylic acid, N,N-dimethyl acrylamide, t-butyl acrylamide, vinyl pyrrolidone, and mixtures thereof, wherein the B monomer units are copolymerizable with the A monomer and C macromonomer units and
      iii) from about 5% to 40% by weight of the copolymer of one or more C macromonomer units selected from the group of polymers consisting of poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate, poly(iso-propyl acrylate), poly(3-methylbutyl acrylate), poly(2-methylpentyl acrylate), poly(nonyl acrylate), poly(octyl acrylate), poly(propyl acrylate), poly(2-ethylhexyl methacrylate), poly(tridecyl methacrylate), poly(hexyl methacrylate), poly(decyl methacrylate), poly(octyl methacrylate), poly(octadecyl methacrylate), poly(dodecyl methacrylate), poly(n-pentyl methacrylate), poly(isobutylene), poly(isoprene), hydrogenated poly(1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly(4,4-dimethyl-1-pentene), poly(iso-butyl vinyl ether), poly(4-t-butyl vinyl benzene-co-2-ethylhexyl acrylate), poly(2-ethylhexyl acrylate-co-octyl acrylamide), poly(2-ethyl vinyl benzene-co-octyl methacrylate), and mixtures thereof wherein the polymers are endcapped by an endcapping group selected from the group consisting of acryloyl, methacryloyl, 2-vinylbenzyl, 3-vinylbenzyl, and 4-vinylbenzyl, wherein the C units are hydrophobic macromonomer units, copolymerizable with the A monomer units and the B monomer units, the C macromonomer units having a number average molecular weight of from about 1,500 to about 50,000; and
   b.) a complexing fatty amine wherein the fatty amine is selected from the group consisting of $C_1$–$C_{22}$ primary amines, $C_1$–$C_{22}$ secondary amines and $C_1$–$C_{22}$ tertiary amines, $C_1$–$C_{22}$ quaternary ammonium salts, $C_1$–$C_{22}$ polyamines, alkyl substituted heterocyclic amines selected from the group consisting of aminoethyl hexadecylimidazoline, N-ethyl morpholine, and N-ethyl piperidine and mixtures thereof, salts thereof and mixtures thereof and wherein the fatty amine forms a complex with the acid functional B monomer units
   wherein the weight ratio of the copolymer to the fatty amine is from about 50:1 to about 1:1; and
B.) a volatile, hydrophobic solvent component for the copolymer complex having a boiling point at 1 atmosphere of about 260° C. or less and a solubility parameter of about 8.5 $(cal/cm^3)^{1/2}$ or less; and
C.) a carrier immiscible with the volatile hydrophobic solvent component wherein the copolymer complex is soluble or dispersible in the volatile, hydrophobic solvent component.

13. A method of treating hair by administering a safe and effective amount of the compositions according to claim 1.

14. A method of treating skin by administering a safe and effective amount of the compositions according to claim 1.

15. A method of making a personal care composition, comprising the steps of:
   a.) preparing a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:
      i) from about 10% to about 99% by weight of the copolymer of one or more hydrophobic A monomer units selected from the group consisting of t-butyl acrylate, t-butyl methacrylate, t-butyl styrene, 2-ethylhexyl methacrylate and mixtures thereof, wherein the A monomer units are copolymerizable with the B monomer and C macromonomer units;
      ii) from about 1% to about 40% by weight of the copolymer of one or more hydrophilic B monomer units selected from the group consisting of acrylic acid, methacrylic acid, N,N-dimethyl acrylamide, t-butyl acrylamide, vinyl pyrrolidone, and mixtures thereof, wherein the B monomer units are copolymerizable with the A monomer and C macromonomer units and
      iii) from about 5% to about 40% by weight of the copolymer of one or more C macromonomer units selected from the group of polymers consisting of poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate, poly(iso-propyl acrylate), poly(3-methylbutyl acrylate), poly(2-methylpentyl acrylate), poly(nonyl acrylate), poly(octyl acrylate), poly(propyl acrylate), poly(2-ethylhexyl methacrylate), poly(tridecyl methacrylate), poly (hexyl methacrylate), poly(decyl methacrylate), poly(octyl methacrylate), poly(octadecyl methacrylate), poly(dodecyl methacrylate), poly(n-pentyl methacrylate), poly(isobutylene), poly(isoprene), hydrogenated poly(1,2-butadiene), hydrogenated poly(1,4 butadiene), hydrogenated poly(isoprene), poly(1,2-butadiene), poly(1-butene), poly(5-methyl-1-hexene), poly(6-methyl-1-heptene), poly(4,4- dimethyl-1-pentene), poly(iso-butyl vinyl ether), poly(4-t-butyl vinyl benzene-co-2-ethylhexyl acrylate), poly(2-ethylhexyl acrylate-co-octyl acrylamide), poly(2-ethyl vinyl benzene-co-octyl methacrylate), and mixtures thereof wherein the polymers are endcapped by an endcapping group selected from the group consisting of acryloyl, methacryloyl, 2-vinylbenzyl, 3-vinylbenzyl, and 4-vinylbenzyl, wherein the C units are hydrophobic macromonomer units, copolymerizable with the A monomer units and the B monomer units, the C macromonomer units having a number average molecular weight of from about 1,500 to about 50,000;

b.) complexing the copolymer with a fatty amine wherein the fatty amine is selected from the group consisting of $C_1$–$C_{22}$ primary amines, $C_1$–$C_{22}$ secondary amities and $C_1$–$C_{22}$ tertiary amines, $C_1$–$C_{22}$ quaternary ammonium salts, $C_1$–$C_{22}$ polyamines, alkyl substituted heterocyclic amines selected from the group consisting of aminoethyl hexadecylimidazoline, N-ethyl morpholine, and N-ethyl piperidine and mixtures thereof, salts thereof and mixtures thereof and wherein the fatty amine forms a complex with the acid functional B monomer units and wherein the weight ratio of the copolymer to the fatty amino is from about 50:1 to about 1:1; and c.) dissolving or dispersing the copolymer complex in a volatile, hydrophobic solvent component having a boiling point at 1 atmosphere of about 260° C. or less and a solubility parameter of about 8.5 $(cal/cm^3)^{1/2}$ or less.

16. A personal care composition which prior to mixing, comprises:

A.) a copolymer complex comprising:
  a.) a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:
    i) from about 10% to about 99% by weight of the copolymer of one or more hydrophobic A monomer units selected from the group consisting of t-butyl acrylate, t-butyl methacrylate, t-butyl styrene, 2-ethylhexyl methacrylate and mixtures thereof, wherein the A monomer units are copolymerizable with the B monomer and C macromonomer units;
    ii) from about 1% to about 40% by weight of the copolymer of one or more hydrophilic B monomer units selected from the group consisting of acrylic acid, methacrylic acid, N,N-dimethyl acrylamide, t-butyl acrylamide, vinyl pyrrolidone, and mixtures thereof, wherein the B monomer units are copolymerizable with the A monomer and C macromonomer units; and
    iii) from about 5% to about 40% by weight of the copolymer of one or more C macromonomer units selected from the group of polymers consisting of poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate), poly(iso-propyl acrylate), poly(3-methylbutyl acrylate), poly(2-methylpentyl acrylate), poly(nonyl acrylate), poly (octyl acrylate), poly(propyl acrylate), poly (2-ethylhexyl methacrylate), poly(tridecyl methacrylate), poly (hexyl methacrylate), poly (decyl methacrylate), poly(octyl methacrylate), poly(octadecyl methacrylate), poly(dodecyl methacrylate), poly(n-pentyl methacrylate), poly (isobutylene), poly(isoprene), hydrogenated poly (1,2-butadiene), hydrogenated poly(1,4-butadiene), hydrogenated poly(isoprene), poly(1, 2-butadiene), poly(1-butene), poly(5-methyl-1-hexene), poly(6-methyl-1-heptene), poly(4,4-dimethyl-1-pentene), poly(iso-butyl vinyl ether), poly(4-t-butyl vinyl benzene-co-2-ethylhexyl acrylate), poly(2-ethylhexyl acrylate-co-octyl acrylamide), poly(2-ethyl vinyl benzene-co-octyl methacrylate), and mixtures thereof wherein the polymers are endcapped by an endcapping group selected from the group consisting of acryloyl, methacryloyl, 2-vinylbenzyl, 3-vinylbenzyl, and 4-vinylbenzyl, wherein the C units are hydrophobic macromonomer units, copolymerizable with the A monomer units and the B monomer units, the C macromonomer units having a number average molecular weight of from about 1,500 to about 50,000; and b.) a complexing fatty amine wherein the fatty amine is selected from the group consisting of $C_1$–$C_{22}$ primary amines, $C_1$–$C_{22}$ secondary amines and $C_1$–$C_{22}$ tertiary amines, $C_1$–$C_{22}$ quaternary ammonium salts, $C_1$–$C_{22}$ polyamines, alkyl substituted heterocyclic amines selected from the group consisting of aminoethyl hexadecylimidazoline, N-ethyl morpholine, and N-ethyl piperidine and mixtures thereof, salts thereof and mixtures thereof and wherein the fatty amine forms a complex with the acid functional B monomer units wherein the weight ratio of the copolymer to the fatty amine is from about 50:1 to about 1:1; and B.) a volatile, hydrophobic solvent component for the copolymer complex having a boiling point at 1 atmosphere of about 260° C. or less and a solubility parameter of about 8.5 $(cal/cm^3)^{1/2}$ or less wherein the copolymer complex is soluble or dispersible in the volatile, hydrophobic solvent component.

17. A hair styling and conditioning composition, comprising:

A.) a copolymer complex comprising:
  a.) a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:
    i) from about 10% to about 99% by weight of the copolymer of one or more hydrophobic A monomer units selected from the group consisting of t-butyl acrylate, t-butyl methacrylate, t-butyl styrene, 2-ethylhexyl methacrylate and mixtures thereof, wherein the A monomer units are copolymerizable with the B monomer and C macromonomer units;
    ii) from about 1% to about 40% by weight of the copolymer of one or more hydrophilic B monomer units selected from the group consisting of acrylic acid, methacrylic acid, N,N-dimethyl acrylamide, t-butyl acrylamide, vinyl pyrrolidone, and mixtures thereof, wherein the B monomer units are copolymerizable with the A monomer and C macromonomer units and iii) from about 5% to about 40% by weight of the copolymer of one or more C macromonomer units selected from the group of polymers consisting of poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate, poly(iso-propyl acrylate), poly(3-methylbutyl acrylate), poly(2-methylpentyl acrylate), poly(nonyl acrylate), poly (octyl acrylate), poly(propyl acrylate), poly (2-ethylhexyl methacrylate), poly(tridecyl methacrylate), poly (hexyl methacrylate), poly (decyl methacrylate), poly(octyl methacrylate), poly(decyl methacrylate), poly(dodecyl methacrylate), poly(n-pentyl methacrylate), poly (isobutylene), poly(isoprene), hydrogenated poly (1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly(4,4-dimethyl-1-pentene), poly(iso-butyl vinyl ether), poly(4-t-butyl vinyl benzene-co-2-ethylhexyl acrylate), poly(2-ethylhexyl acrylate-co-octyl acrylamide), poly(2-ethyl vinyl benzene-co-octyl methacrylate), and mixtures thereof wherein the polymers are endcapped by an endcapping group selected from the group consisting of acryloyl, methacryloyl, 2-vinylbenzyl, 3-vinylbenzyl, and 4-vinylbenzyl, wherein the C units are hydrophobic macromonomer units, copolymerizable with the A monomer units and the B monomer units, the C macromonomer units having a number average molecular weight of from about 1,500 to about 50,000; and b.) a complexing fatty amine wherein the fatty amine is selected from the group consisting of $C_1$–$C_{22}$ primary amines, $C_1$–$C_{22}$ secondary amines and $C_1$–$C_{22}$ tertiary amines, $C_1$–$C_{22}$ quaternary ammonium salts, $C_1$–$C_{22}$ polyamines, alkyl substituted heterocyclic amines selected from the group consisting of aminoethyl hexadecylimidazoline, N-ethyl morpholine, and N-ethyl piperidine and mixtures thereof, salts thereof and mixtures thereof and wherein the fatty amine forms a complex with the acid functional B monomer units wherein the weight ratio of the copolymer tote fatty amine is from about 50:1 to about 1:1; and B.) a volatile, hydrophobic solvent component for the copolymer complex having a boiling point at 1 atmosphere of about 260° C. or less and a solubility parameter of about 8.5 $(cal/cm^3)^{1/2}$ or less wherein the copolymer complex is soluble or dispersible in the volatile, hydrophobic solvent component and wherein the copolymer complex and volatile, hydrophobic solvent component mixture has a viscosity of above about 5,000 cps.

18. A hair care composition, comprising:

I.) a hair styling and conditioning component, comprising:

A.) a copolymer complex comprising:

a.) a copolymer having a backbone formed from the copolymerization of repeating A monomer and B monomer units wherein the backbone has optionally grafted to it hydrophobic C macromonomer units wherein the copolymer is prepared by the polymerization combination of the following relative weight percentages of the A, B, and C units:

i) from about 10% to about 99% by weight of the copolymer of one or more hydrophobic A monomer units selected from the group consisting of t-butyl acrylate, t-butyl methacrylate, t-butyl styrene, 2-ethylhexyl methacrylate and mixtures thereof, wherein the A monomer units are copolymerizable with the B monomer and C macromonomer units;

ii) from about 1% to about 40% by weight of the copolymer of one or more hydrophilic B monomer units selected from the group consisting of acrylic acid, methacrylic acid, N,N-dimethyl acrylamide, t-butyl acrylamide, vinyl pyrrolidone, and mixtures thereof, wherein the B monomer units are copolymerizable with the A monomer and C macromonomer units; and iii) from about 5% to about 40% by weight of the copolymer of one or more C macromonomer units selected from the group of polymers consisting of poly(n-butyl acrylate), poly(dodecyl acrylate), poly(2-ethylhexyl acrylate), poly(2-ethylbutyl acrylate), poly(n-ethyl acrylate), poly(n-heptyl acrylate), poly(n-hexyl acrylate), poly(iso-butyl acrylate), poly(iso-decyl acrylate, poly(iso-propyl acrylate), poly(3-methylbutyl acrylate), poly(2-methylpentyl acrylate), poly(nonyl acrylate), poly (octyl acrylate), poly(propyl acrylate), poly (2-ethylhexyl methacrylate), poly(tridecyl methacrylate), poly (hexyl methacrylate), poly (decyl methacrylate), poly(octyl methacrylate), poly(octadecyl methacrylate), poly(dodecyl methacrylate), poly(n-pentyl methacrylate), poly (isobutylene), poly(isoprene), hydrogenated poly (1,2-butadiene), hydrogenated poly(1,4-butadiene), hydrogenated poly(isoprene), poly(1,2-butadiene), poly(1-butene), poly(5-methyl-1-hexene), poly(6-methyl-1-heptene), poly(4,4-dimethyl-1-pentene), poly(iso-butyl vinyl ether), poly(4-t-butyl vinyl benzene-co-2-ethylhexyl acrylate), poly(2-ethylhexyl acrylate-co-octyl acrylamide), poly(2-ethyl vinyl benzene-co-octyl methacrylate), and mixtures thereof wherein the polymers are endcapped by an endcapping group selected from the group consisting of acryloyl, methacryloyl, 2-vinylbenzyl, 3-vinylbenzyl, and 4-vinylbenzyl, wherein the C units are hydrophobic macromonomer units, copolymerizable with the A monomer units and the B monomer units, the C macromonomer units having a number average molecular weight of from about 1,500 to about 50,000; and b.) a complexing fatty amine wherein the fatty amine is selected from the group consisting of $C_1$–$C_{22}$ primary amines, $C_1$–$C_{22}$ secondary amines and $C_1$–$C_{22}$ tertiary amines, $C_1$–$C_{22}$ quaternary ammonium salts, $C_1$–$C_{22}$ polyamines, alkyl substituted heterocyclic amines selected from the group consisting of aminoethyl hexadecylimidazoline, N-ethyl morpholine, and N-ethyl piperidine and mixtures thereof, salts thereof and mixtures thereof and wherein the fatty amine forms a complex with the acid functional B monomer units wherein the weight ratio of the copolymer to the fatty amine is from about 50:1 to about 1:1; and B.) a volatile, hydrophobic solvent component for the copolymer complex having a boiling point at 1 atmosphere of about 260° C. or less and a solubility parameter of about 8.5 $(cal/cm^3)^{1/2}$ or less and wherein the copolymer complex is soluble or dispersible in the volatile, hydrophobic solvent component wherein the copolymer complex and volatile, hydrophobic solvent component mixture has a viscosity of above about 5,000 cps; and II.) a carrier immiscible with the volatile hydrophobic solvent component.

* * * * *